(12) United States Patent
Miller

(10) Patent No.: US 7,101,356 B2
(45) Date of Patent: Sep. 5, 2006

(54) IMPLANTABLE VASCULAR ACCESS DEVICE

(76) Inventor: Stuart H. Miller, 16 E. Eighth St., Clifton, NJ (US) 07011-1102

( * ) Notice: Subject to any disclaimer, the term of this patent is extended or adjusted under 35 U.S.C. 154(b) by 899 days.

(21) Appl. No.: 10/102,934

(22) Filed: Mar. 22, 2002

(65) Prior Publication Data

US 2004/0193106 A1  Sep. 30, 2004

Related U.S. Application Data

(60) Provisional application No. 60/277,955, filed on Mar. 23, 2001.

(51) Int. Cl.
*A61M 39/04* (2006.01)

(52) U.S. Cl. ............ 604/288.02; 604/288.01; 604/288.04; 604/93.01

(58) Field of Classification Search ........ 604/93.01, 604/288.01, 288.02, 288.04, 285, 175
See application file for complete search history.

(56) References Cited

U.S. PATENT DOCUMENTS

| | | | |
|---|---|---|---|
| 4,692,146 A | | 9/1987 | Hilger |
| 5,041,098 A | | 8/1991 | Loiterman et al. |
| 5,704,915 A | * | 1/1998 | Melsky et al. ............ 604/175 |
| 5,833,654 A | * | 11/1998 | Powers et al. .......... 604/93.01 |
| 5,848,989 A | | 12/1998 | Villani |
| 5,944,688 A | | 8/1999 | Lois |
| 6,086,555 A | * | 7/2000 | Eliasen et al. ......... 604/93.01 |
| 6,231,541 B1 | * | 5/2001 | Kawamura ............... 604/93.01 |
| 6,582,409 B1 | * | 6/2003 | Squitieri ................ 604/288.01 |
| 6,929,631 B1 | * | 8/2005 | Brugger et al. ............ 604/502 |
| 2001/0056266 A1 | * | 12/2001 | Tallarida et al. ....... 604/288.02 |

* cited by examiner

*Primary Examiner*—Nickolas D. Lucchesi
*Assistant Examiner*—Melissa A. McCorkle
(74) *Attorney, Agent, or Firm*—Welsh & Flaxman LLC

(57) ABSTRACT

An implantable dual chambered catheter device includes a first chamber and a second chamber integrally joined. The first chamber includes a hollow first elastomeric member contained within a first slotted outer housing. A first end of the first elastomeric member is fitted with a first end cap shaped and dimensioned to accept conventional catheter tubes and the second end of the first elastomeric member is closed. The second chamber includes a hollow second elastomeric member contained within a second slotted outer housing. A first end of the second elastomeric member is fitted with a second end cap shaped and dimensioned to accept conventional catheter tubes and the second end of the second elastomeric member is closed. Needle access to the first and second chambers of the implantable catheter device is through respective slots formed within the first and second outer housings.

20 Claims, 24 Drawing Sheets

ELASTOMERIC SEPTUM PER VILLANI US PATENT # 5848989
AXISYMMETRICAL MODEL W/LENGTH DIAMETER RATIO =1
ONLY ONE HALF OF MODEL IS SHOWN (SYMMETRY IS ABOUT Y AXIS)
UNDEFORMED MODEL HAS 0.002 IN RADIAL HOLE THROUGH CENTER
DEFORMED GEOMETRY W/UNDEFORMED OVERLAY

FIG.3
ELASTOMERIC SEPTUM PER VILLANI US PATENT # 5848989
AXISYMMETRICAL MODEL W/LENGTH DIAMETER RATIO =1
ONLY ONE HALF OF MODEL IS SHOWN (SYMMETRY IS ABOUT Y AXIS)
UNDEFORMED MODEL HAS 0.002 IN RADIAL HOLE THROUGH CENTER
RADIAL DISPLACEMENT AT THE 0.002 INCH RADIAL HOLE
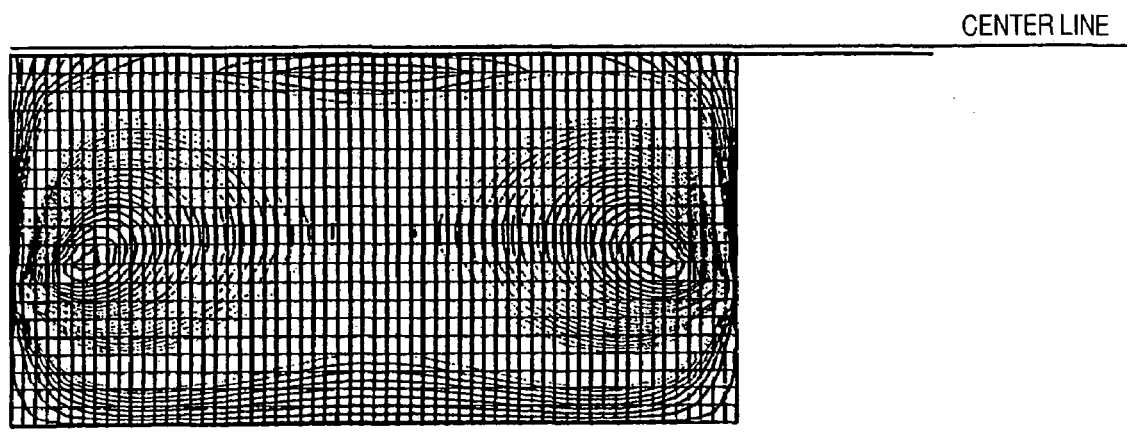
CENTER LINE
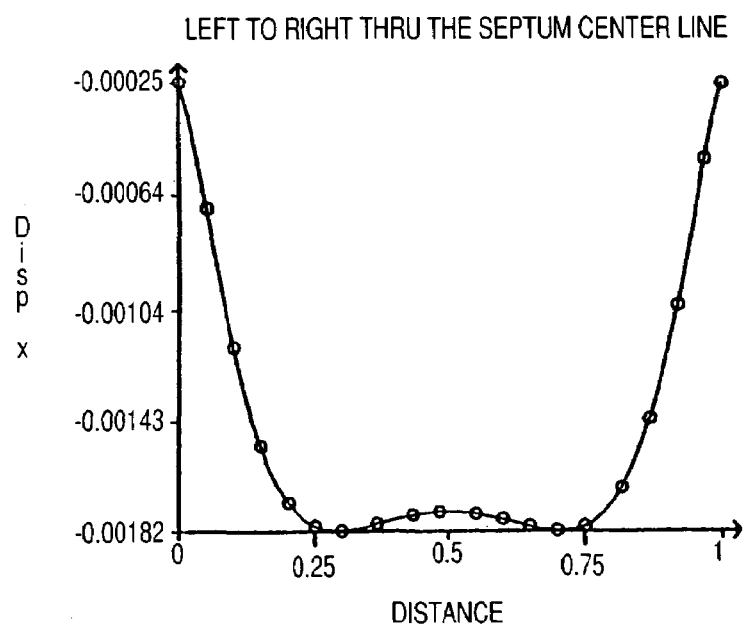
LEFT TO RIGHT THRU THE SEPTUM CENTER LINE
DISTANCE

FIG.4
ELASTOMERIC SEPTUM PER VILLANI US PATENT # 5848989
AXISYMMETRICAL MODEL W/LENGTH DIAMETER RATIO =1
RADIAL DISPLACEMENT AT THE 0.001 INCH RADIAL HOLE
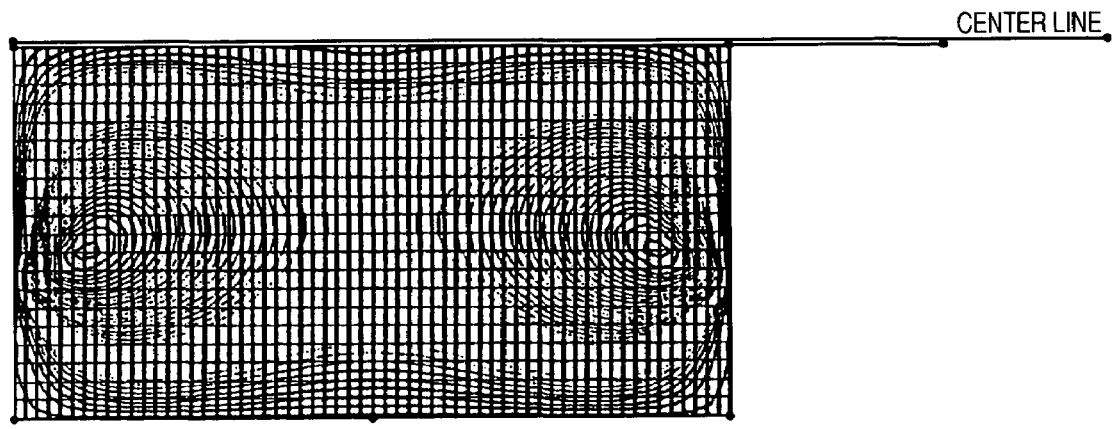
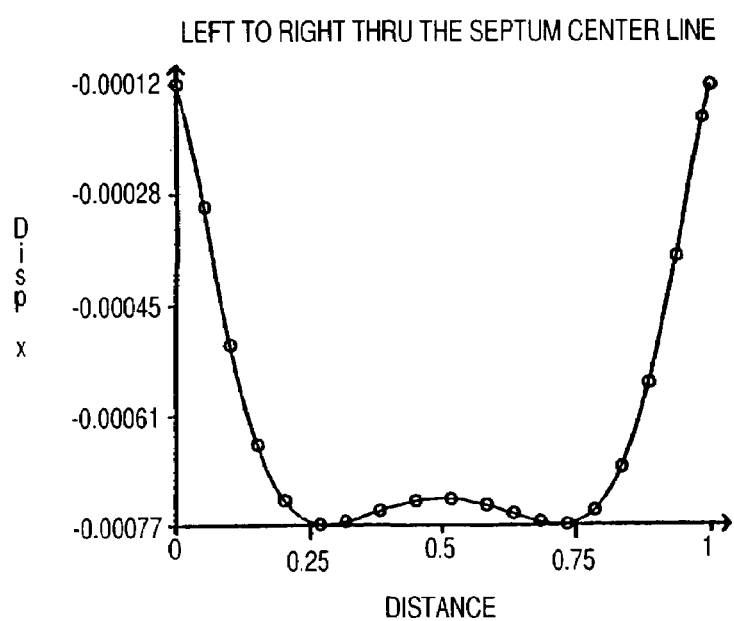

FIG.5
ELASTOMERIC SEPTUM PER VILLANI US PATENT # 5848989
AXISYMMETRICAL MODEL W/LENGTH DIAMETER RATIO =1
RADIAL DISPLACEMENT AT THE 0.0005 INCH RADIAL HOLE
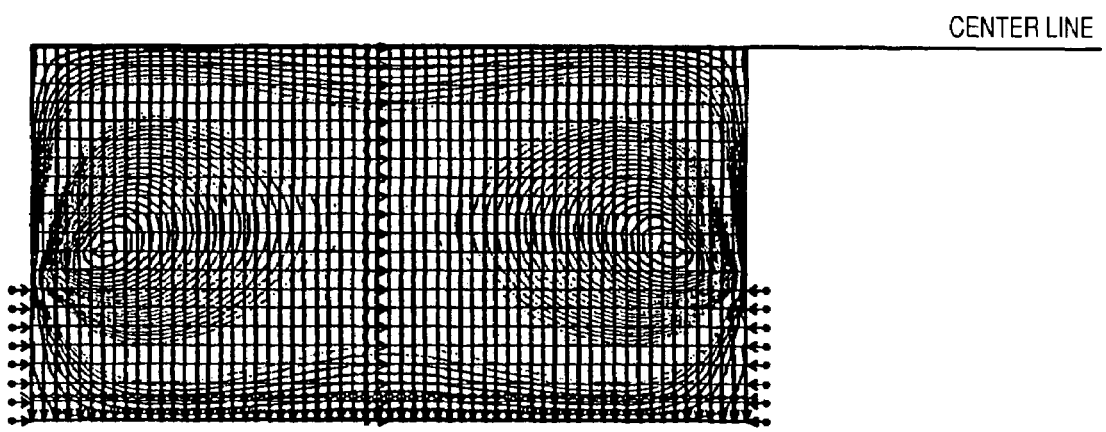
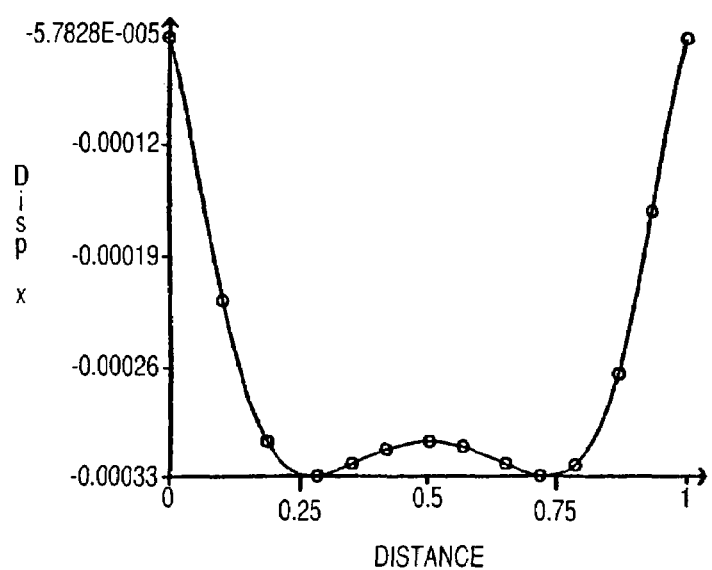

FIG.6
ELASTOMERIC SEPTUM PER VILLANI US PATENT # 5848989
AXISYMMETRICAL MODEL W/LENGTH DIAMETER RATIO =1
RADIAL DISPLACEMENT AT THE 0.0001 INCH RADIAL HOLE
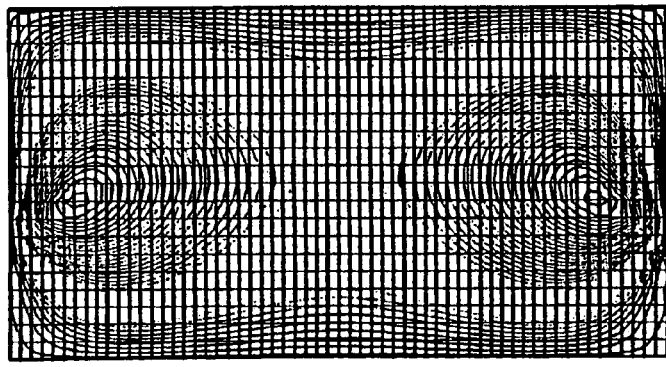
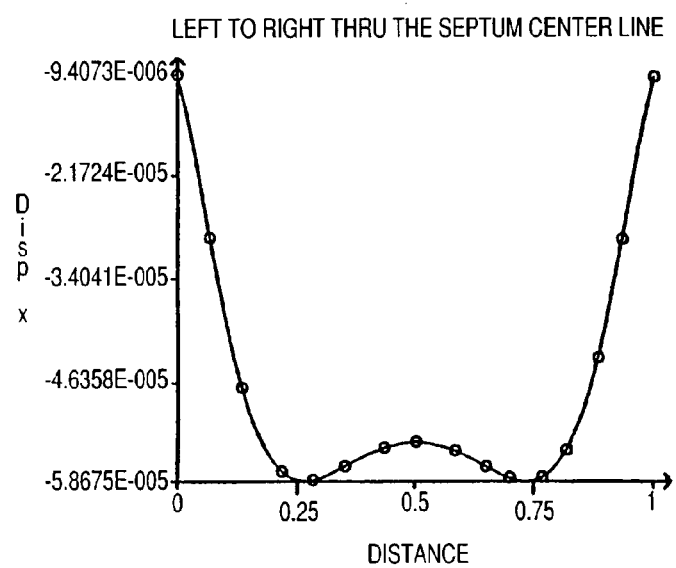

3D MODEL OF THE SEPTUM IN VILLANI US PATENT # 5848989
LENGTH / DIAMETER RATIO = 1
0.002 IN RADIUS HOLE THRU CENTER

3D MODEL OF THE SEPTUM IN VILLANI US PATENT # 5848989
LENGTH / DIAMETER RATIO = 1
0.002 IN RADIUS HOLE THRU CENTER
DEFORMED GEOMETRY FOR AN AXIAL COMPRESSION = 0.025 INCHES

3D MODEL OF THE SEPTUM IN VILLANI US PATENT # 5848989
LENGTH / DIAMETER RATIO = 1
0.002 IN RADIUS HOLE THRU CENTER
DEFORMED GEOMETRY FOR AN AXIAL COMPRESSION = 0.025 INCHES

ONE TUBE OF A DUAL TUBE CATHETER (0.3135 IN ID x 0.500 IN OD)
FOR 7 FRENCH MAX CATHETER SIZE
CONSTRAINTS & LOADING
RADIAL DEFORMATION - 0.010 IN & INTERNAL PRESSURE = 300 MM HG

ONE TUBE OF A DUAL TUBE CATHETER (0.3135 IN ID x 0.500 IN OD)
FOR 7 FRENCH MAX CATHETER SIZE
RADIAL DEFORMATION - 0.010 IN & INTERNAL PRESSURE = 300 MM HG
DEFORMED GEOMETRY WITH UNDEFORMED OVERLAY

ONE TUBE OF A DUAL TUBE CATHETER (0.3135 IN ID x 0.500 IN OD) FOR 7 FRENCH MAX CATHETER SIZE

ONE TUBE OF A DUAL TUBE CATHETER (0.3135 IN ID x 0.500 IN OD)
FOR 7 FRENCH MAX CATHETER SIZE
RADIAL DEFORMATION - 0.010 IN & INTERNAL PRESSURE = 300 MM HG
MINIMUM PRINCIPAL STRESS AT 300 MM HG INTERNAL PRESSURE

ONE TUBE OF A DUAL TUBE CATHETER (0.3135 IN ID x 0.500 IN OD)
FOR 7 FRENCH MAX CATHETER SIZE

ONE TUBE OF A DUAL TUBE CATHETER (0.3135 IN ID x 0.500 IN OD)
FOR 7 FRENCH MAX CATHETER SIZE
RADIAL DEFORMATION - 0.010 IN & INTERNAL PRESSURE = 300 MM HG
MINIMUM PRINCIPAL STRESS AT 300 MM HG INTERNAL PRESSURE

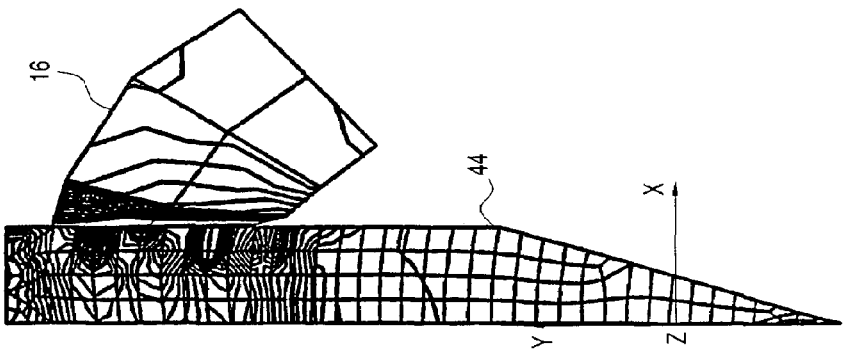
FIG.24 MODEL OF THE CATHETER PROJECTION BEING PENETRATED BY A 7 FRENCH DIAMETER OBJECT VON MISES STRESS AT FULL PENETRATION
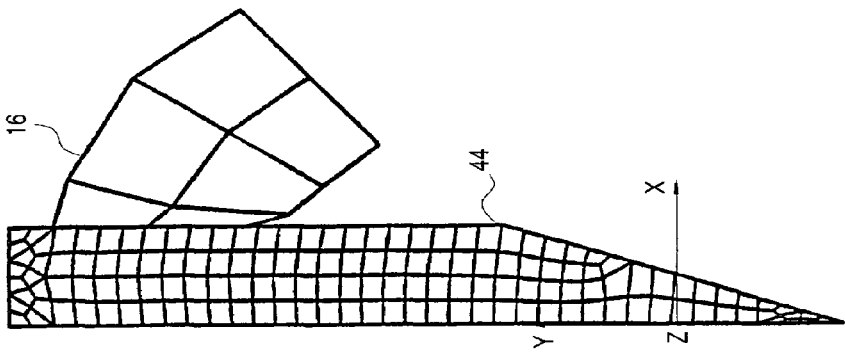
FIG.23 MODEL OF THE CATHETER PROJECTION BEING PENETRATED BY A 7 FRENCH DIAMETER OBJECT DEFORMED GEOMETRY AT FULL PENETRATION
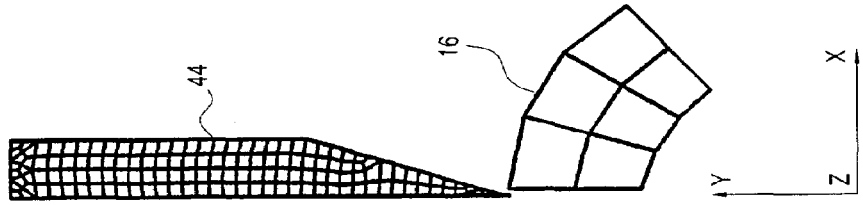
FIG.22 MODEL OF THE CATHETER PROJECTION BEING PENETRATED BY A 7 FRENCH DIAMETER OBJECT Number of Single Punctures & % change ONE TUBE OF A DUAL TUBE CATHETER (0.3135 IN ID x 0.500 IN OD)
MINIMUM PRINCIPAL STRESS AT 300 MM HG INTERNAL PRESSURE ONE TUBE OF A DUAL TUBE CATHETER (0.3135 IN ID x 0.500 IN OD)
MINIMUM PRINCIPAL STRESS AT 300 MM HG INTERNAL PRESSURE

IMPLANTABLE VASCULAR ACCESS DEVICE

CROSS REFERENCE TO RELATED APPLICATION

This application is based upon U.S. Provisional Patent Application Ser. No. 60/277,955, filed Mar. 23, 2001, entitled "IMPLANTABLE CATHETER ASSEMBLY FOR HEMODIALYSIS", which is currently pending.

BACKGROUND OF THE INVENTION

1. Field of the Invention

The invention relates to an implantable catheter assembly for hemodialysis. More particularly, the invention relates to an implantable catheter assembly providing long or short term access via a needle wherein a puncture region is readily sealed after removal of the puncturing needle.

2. Description of the Prior Art

Patients with renal failure face certain death unless managed by either hemodialysis or peritoneal dialysis. Renal transplantation is the best, albeit less available, solution to this problem. As a result, various dialysis solutions have been developed. One current hemodialysis solution includes the surgical creation of an arterial to venous fistula using either native vein or polyfluorotetraethylene (PTFE) prosthetic vein. However, fistulas such as these are prone to clotting and have an average life span of only 1 to 1½ years.

A recent alternative to surgically placed grafts is a fluoroscopically placed hemodialysis catheter, or vascular access device. Vascular access devices are placed in an outpatient setting, can remain in place for months, and provide excellent flow rates necessary for hemodialysis. Unfortunately, infection, skin loosening, and the possibility of catheters coming apart have resulted in great expense, as well as patient morbidity and mortality.

Such vascular access devices are disclosed in prior art. For example, attention is directed to the devices disclosed in U.S. Pat. No. 4,692,146 to Hilger, U.S. Pat. No. 5,041,098 to Loiterman et al., U.S. Pat. No. 5,848,989 to Villani and U.S. Pat. No. 5,944,688 to Lois. In general, Loiterman discloses penetrating a "resealable" elastomeric septum with a large diameter needle. However, Loiterman does not mention how the resealing is accomplished.

Experiments have shown that repetitive punctures of a septum with large diameter needles will result in the leakage of blood through the septum. With this in mind, nowhere does Loiterman discuss how to achieve a septum seal after repetitive punctures with a large diameter needle. Loiterman merely discloses the septum as comprising a self-sealing material. However, it is highly unlikely that the structure disclosed by Loiterman would in fact work as proposed for an extended period of time.

Lois, like Loiterman, only refers to the disclosed septum as being constructed of a "self-sealing material". Lois provides no details as to making certain the sealing is accomplished after multiple punctures with a large bore needle.

Further, and with reference to Villani and Hilger, they both provide an elastomeric septum having a similar design. Generally, a cylindrical elastomeric plug is compressed axially along a radial portion of the plug. This compresses the plug axially along a small radial portion at the outside diameter of the plug, producing convex bulges at both ends of the plug. In this way, both Villani and Hilger attempt to provide sealing of the plug by axial compression while simultaneously providing needle access through the plug. A finite element analysis (see FIGS. 1 to 10) of the Villani and Hilger septums clearly shows that repetitive needle punctures in a septum of this design will not seal. That is, the stress distribution within the septum tends to keep the hole open, thereby permitting the passage of blood through the open hole (which is highly undesirable).

The finite element analysis of the Villani and Hilger type designs was conducted to determine whether or not sealing is obtained once a hole is produced in the septum. The criterion upon which sealing is determined is the deformed geometry of the plug in the region of the hole. As those skilled in the art will well appreciate, finite element analysis is a universally accepted method for conducting structural analysis. It enables one skilled in the art to determine the deformation and stress distributions in an engineered product. With this in mind, finite element analysis of the designs disclosed by Villani and Hilger was conducted to evaluate their sealing capabilities. The results of the study show that it is possible to produce holes in the septums disclosed by Villani and Hilger which will not seal, that is, holes in the septum will remain open permitting the passage of blood through the septum. In fact, five studies were conducted. Four models were asymmetrical and the fifth model was three dimensional.

FIG. 1 shows an asymmetrical model of the Villani/Hilger design. The model is symmetrical about the center line and has a 0.002" radial hole in the septum.

FIG. 2 shows the deformed geometry of the septum when loaded as per the Villani/Hilger patents. Note that the analysis correctly shows the convex geometry produced in the septum as a result of the loading. The model clearly shows that the hole does not close. FIG. 2A is a close up of the central portion of the model shown in FIG. 2. The Figure shows the deformed geometry of the model along with the center line and the undeformed 0.002" radius of the hole. The close up in FIG. 2A shows the open hole as the distance between the central line and the upper edge of the deformed model. The graph in FIG. 3 shows the radial displacement of the entire length of the hole in the deformed septum. The undeformed hole radius is 0.002". The two ends of the graph show that a 0.002" deformed hole at the ends of the septum will only close by 0.00025", i.e., the radius of the open hole at the ends of the septum is 0.002"−0.00025"=0.00175".

In a similar fashion, the radius of the hole may also be determined through the entire length of the septum. Note that the "distance" scale on the graph represents the fraction of the distance along the length of the septum. Zero and 1 are the two ends of the septum; 0.25 is a point ¼ of the distance from the left end of the septum, etc. Note that the greatest closure of the 0.002" hole occurs at distances of 0.25 and 0.75. At these two locations, a hole of radius 0.002"−0.00182"=0.00018" still exists. The study, therefore, shows that a hole in the septum with a radius of 0.002" will remain open with a radius value ranging from approximately 0.00018" to 0.00175".

The study was repeated for initial hole diameters of 0.001", 0.0005" and 0.0001". The results are shown in FIGS. 4, 5 and 6. Note that even if the initial hole in the septum has a radius of 0.0001", the hole in the deformed septum remains open with a radius of at least 0.000041".

A three-dimensional FEA model of the Villani/Hilger septum was then studied for verification purposes. The undeformed model is shown in FIG. 7. The model has a central hole of radius 0.002". The deformed geometry of the septum is shown in FIGS. 8 and 9. Note that the model clearly shows the convex geometry at the ends of the septum in the deformed state. FIG. 10 is a view along the Z-axis of the deformed septum, i.e., looking directly down the deformed hole. From FIG. 10 we see that the hole closes slightly at the ends of the septum FIG. 10 also clearly shows an open hole completely through the septum through which undesirable blood flow may exist. The three-dimensional model results verify the two-dimensional model results.

Villani and Hilger attempt to seal the needle puncture holes by compressing the septum axially. The finite element analysis of the Villani/Hilger design shows that the septum cannot be effectively sealed using this design. Once a hole has been established in the septum by repeated needle punctures, the hole remains open and will permit an undesirable blood flow passage through the septum.

In summary, the present invention provides a resealable vascular access device substantially distinct from those disclosed in the prior art. With this in mind, the present invention overcomes the prior art by providing an implantable catheter device resealable so as to permit multiple punctures by large diameter needles.

SUMMARY OF THE INVENTION

It is, therefore, an object of the present invention to provide an implantable dual chambered catheter device. The device includes a first chamber and a second chamber integrally joined. The first chamber includes a hollow first elastomeric member contained within a first slotted outer housing. A first end of the first elastomeric member is fitted with a first end cap shaped and dimensioned to accept conventional catheter tubes and the second end of the first elastomeric member is closed. The second chamber includes a hollow second elastomeric member contained within a second slotted outer housing. A first end of the second elastomeric member is fitted with a second end cap shaped and dimensioned to accept conventional catheter tubes and the second end of the second elastomeric member is closed. Needle access to the first and second chambers of the implantable catheter device is through respective slots formed within the first and second outer housings.

It is also an object of the present invention to provide a catheter device wherein the first and second end caps are titanium.

It is another object of the present invention to provide a catheter device wherein the first and second chambers are tubular.

It is a further object of the present invention to provide a catheter device wherein the first and second elastomeric members are cylindrical.

It is also another object of the present invention to provide a catheter device wherein the first and second slotted outer housings are cylindrical.

It is still another object of the present invention to provide a catheter device wherein the first and second elastomeric members are respectively held within the first and second outer housings under radial compressive stresses.

It is yet a further object of the present invention to provide a catheter device wherein the first and second slotted outer housings are titanium.

It is also an object of the present invention to provide a catheter device wherein compressive stresses applied to the first and second elastomeric members create a bulge in the first and second elastomeric members along respective slots formed in the first and second outer housings.

It is another object of the present invention to provide a catheter device wherein the applied circumferential stresses range from approximately 6 psi to 87 psi.

It is a further object of the present invention to provide a catheter device wherein the radial compressive stresses applied to the first and second elastomeric members provide compressive circumferential hoop stresses in the first and second elastomeric member which serve to seal needle holes in the first and second elastomeric members following needle withdrawal.

It is also a further object of the present invention to provide a catheter device wherein the first and second elastomeric members include uncompressed outer dimensions slightly larger than the inner dimensions of the respective first and second outer housings in which they are positioned.

It is another object of the present invention to provide a catheter device wherein the first and second elastomeric members are constructed from implantable grade silicone rubber.

It is still another object of the present invention to provide a catheter device wherein the first and second elastomeric members have a durometer of 60 Shore A.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 1 to 10 show the results of finite element analysis for prior art septum constructions.

FIG. 22 shows a portion of the elastomeric portion about to be penetrated by a needle.

FIG. 23 shows the deformed geometry of the elastomer.

FIG. 24 shows the Von Mises stress distribution in the elastomer.

DESCRIPTION OF THE PREFERRED EMBODIMENTS

Figure 1:
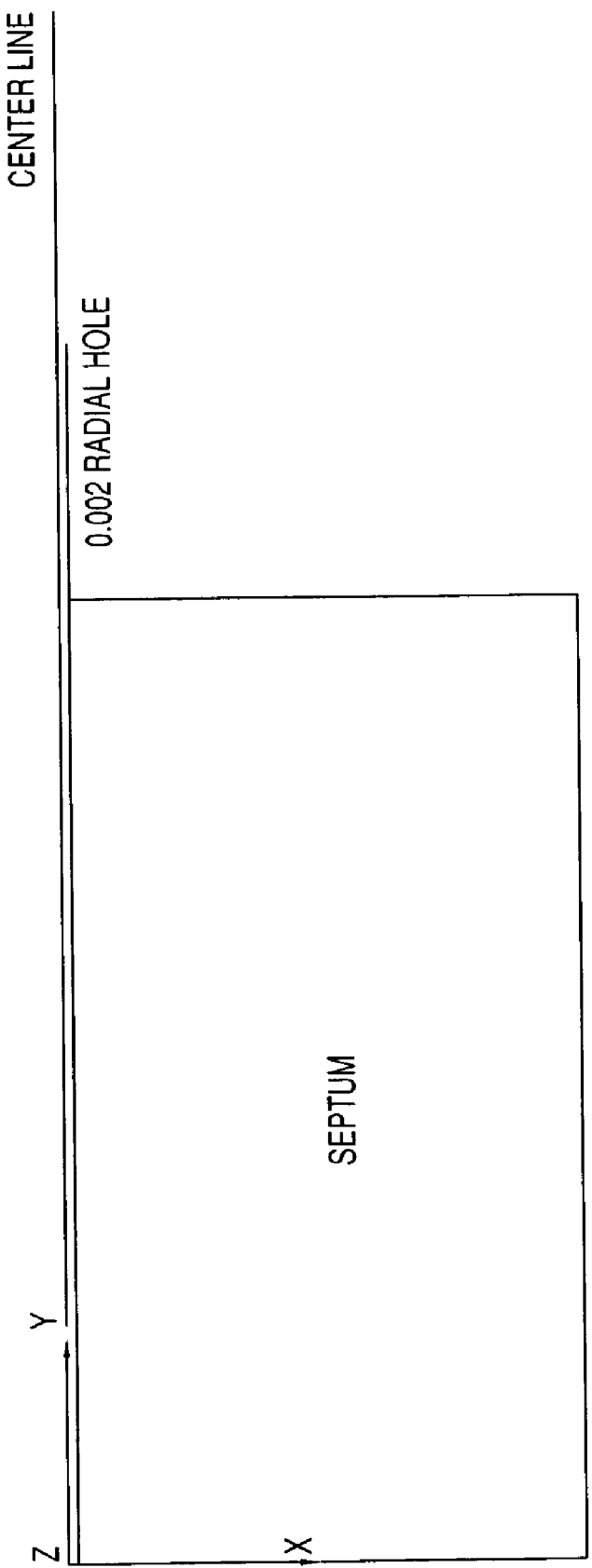
Figure 2:
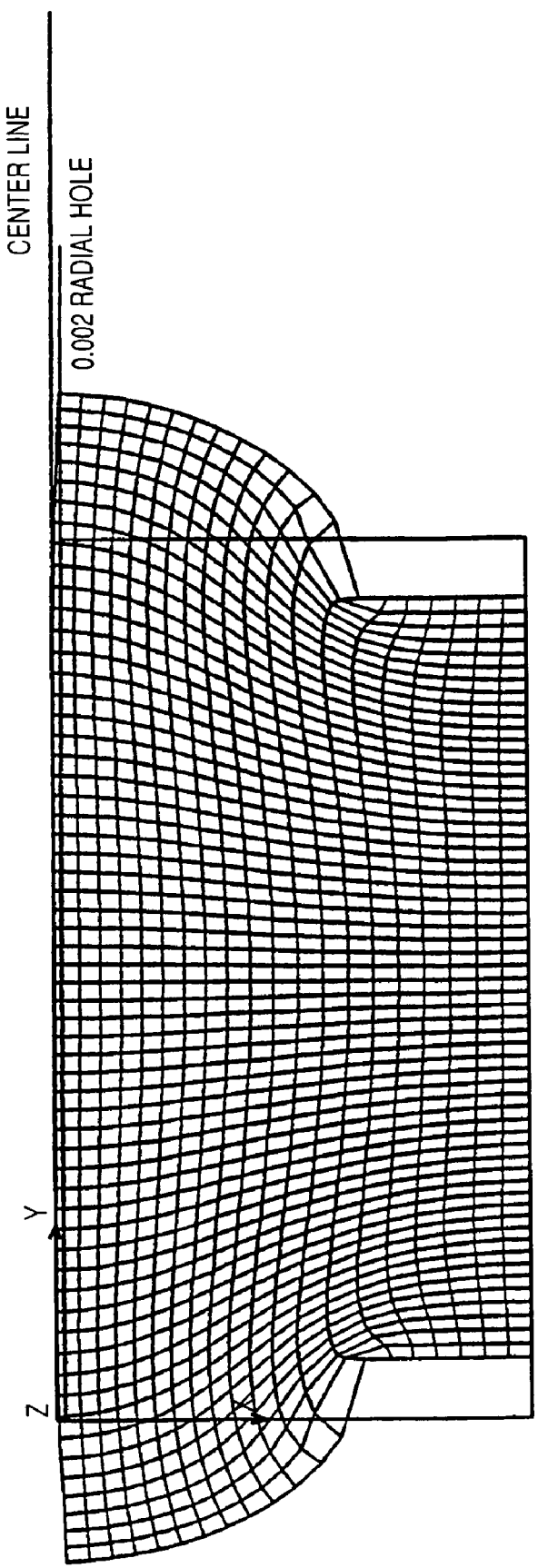
Figure 2A:
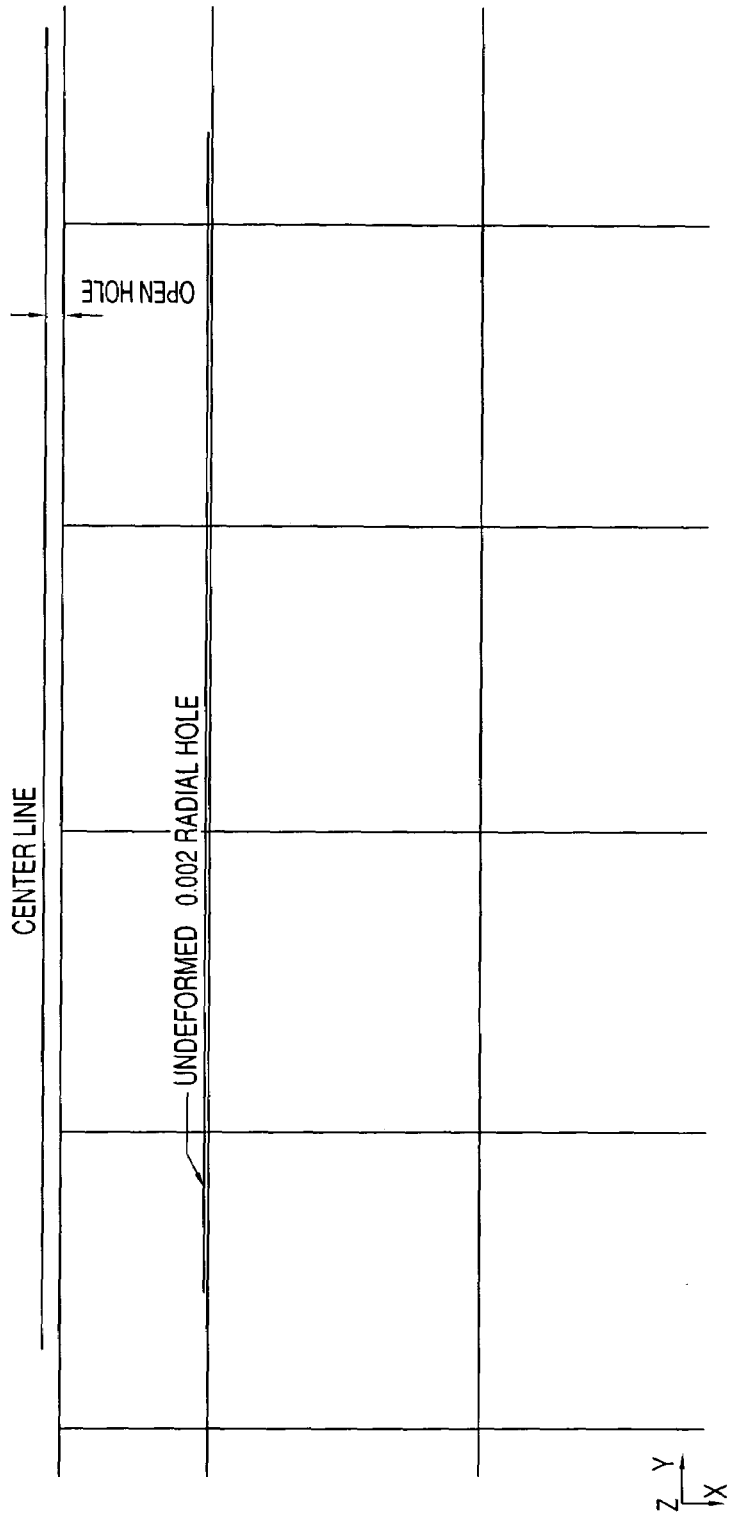
Figure 7:
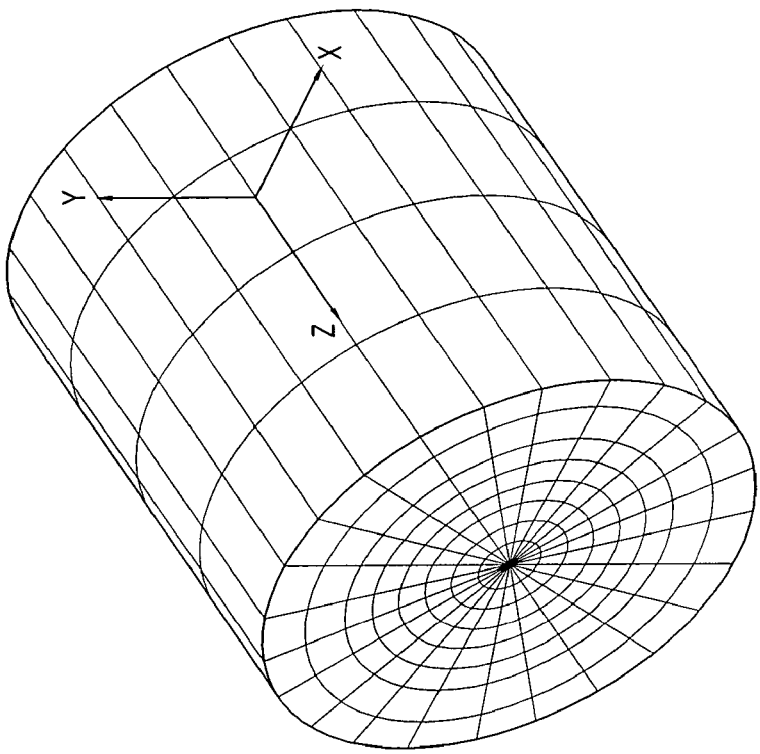
Figure 8:
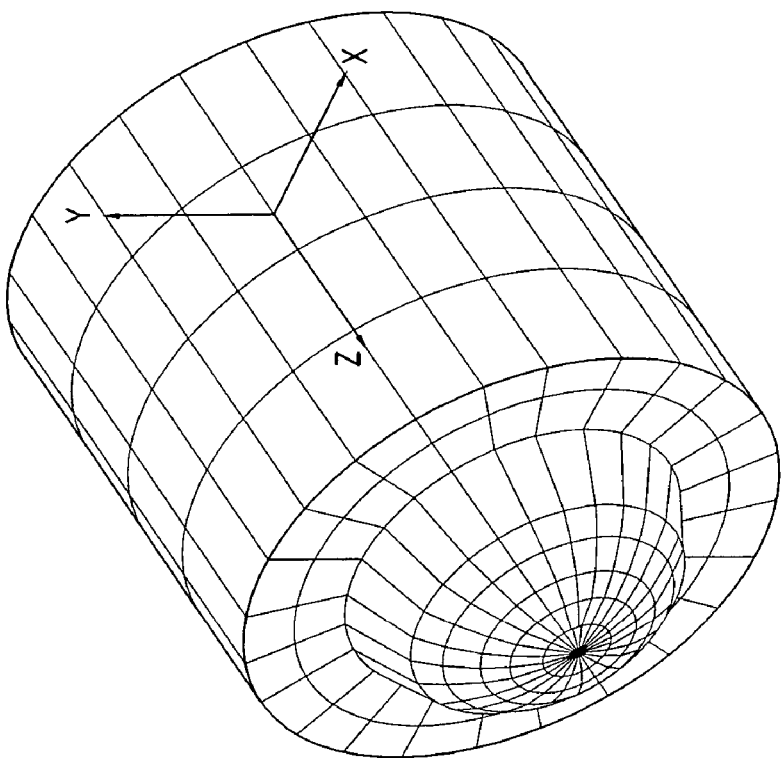
Figure 9:
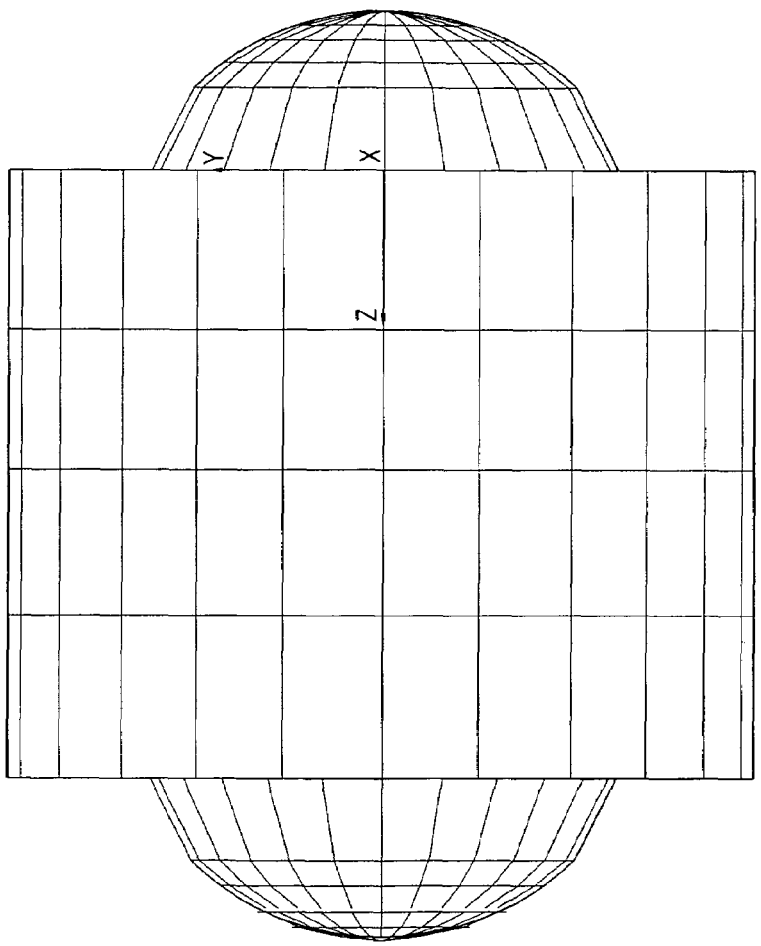
Figure 10:
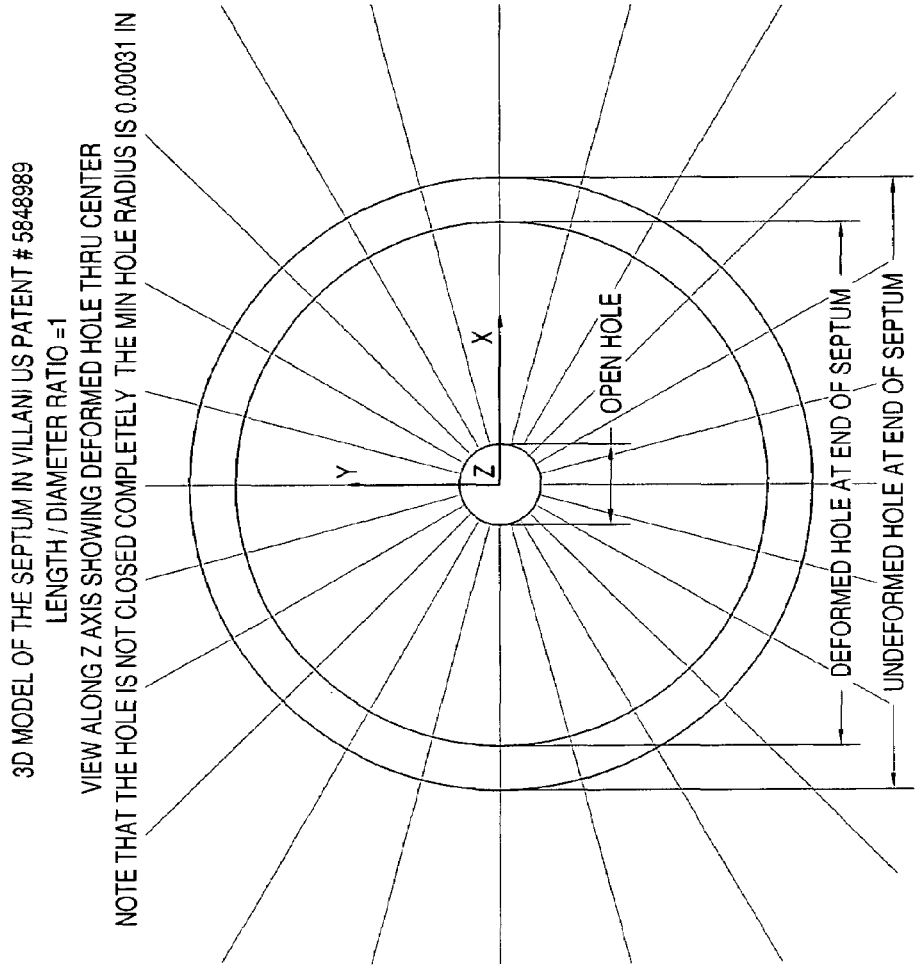
Figure 11:
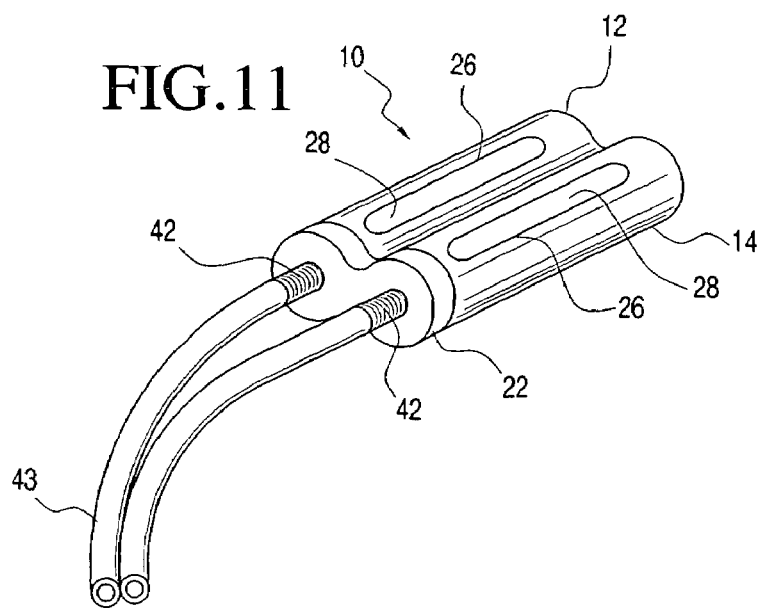
FIG. 11 is a perspective view of the present implantable catheter device.
Figure 12:
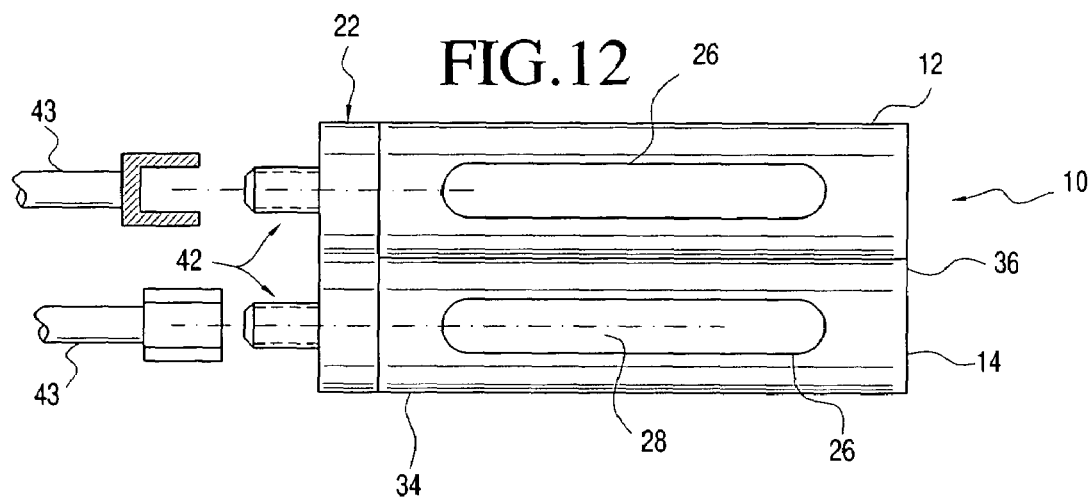
FIG. 12 is a top view of the present implantable catheter device.
Figure 13:
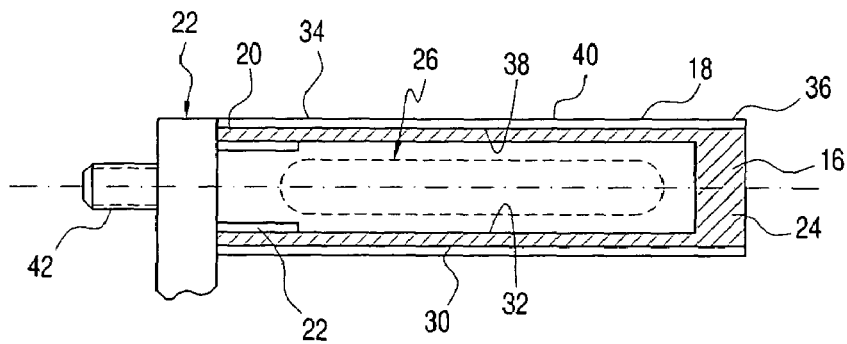
FIG. 13 is a cross sectional view of the first tubular chamber of the present implantable catheter device
Figure 14:
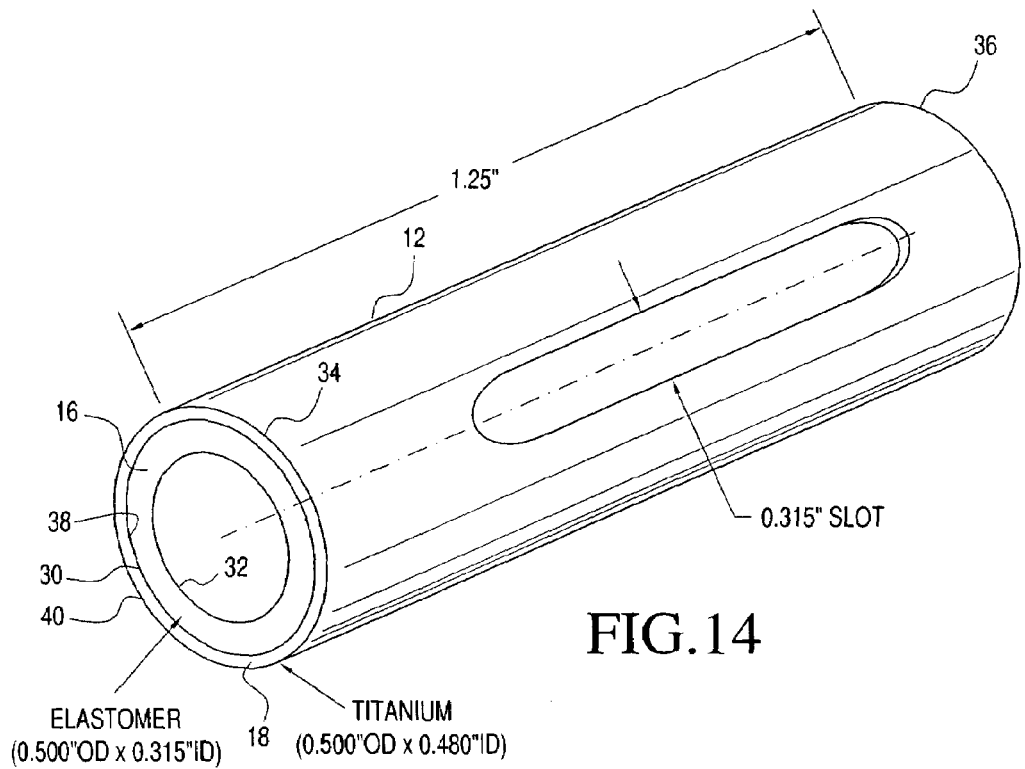
FIG. 14 is a perspective view of the first tubular chamber of the implantable catheter device with the end 22 removed.

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

With reference to FIGS. 11, 12, 13 and 14, an implantable dual chambered catheter device 10 is disclosed. The catheter device 10 is a dual chambered device and includes first and second tubular chambers 12, 14 joined to form a single implantable catheter device 10. Each of the tubular chambers 12, 14 is generally composed of an elastomeric cylindrical member 16 contained within a slotted titanium outer cylinder 18. Since the first and second tubular chambers 12, 14 are identical, similar reference numerals are used to designate similar components of each chamber.

At first end 20 of each elastomeric cylindrical member 16 is fitted with a titanium end cap 22 shaped and dimensioned to accept conventional catheter tubes. An end cap 22 is positioned within each of the elastomeric cylindrical members, and is preferably secured therein via conventional coupling techniques, such as, bonding and compression fitting. Specifically, and in accordance with a preferred embodiment of the present invention, the open first end 20 of the elastomeric cylindrical member 16 includes a molded in, cylindrical end cap 22 containing male threads 42 to which the catheter tubes 43 are selectively attached in the manner discussed below in greater detail. The second end 24 of each elastomeric cylindrical member 16 is molded such that it is closed.

Figure 15:
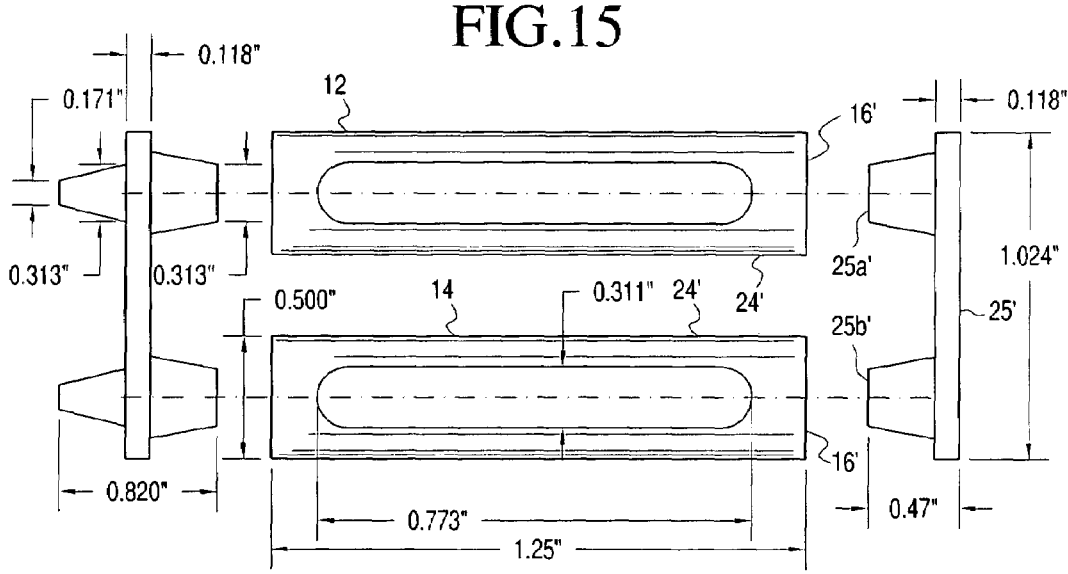
FIG. 15 is an exploded view of a further embodiment of the present implantable catheter device.

With reference to FIG. 15, and in accordance with a further embodiment of the present invention, the second end 24' of each of the elastomeric cylindrical members 16' maybe closed through the use of a plug 25' adapted to frictionally fit within the open second ends 24' of the cylindrical members 16' and thereby close off the second ends 24' thereof. The plug 25' is formed with dual plugging members 25a' and 25b' as to simultaneously seal both the first and second tubular chambers 12', 14'

The first and second tubular chambers 12, 14 are held together by suitable means to form the single, implantable catheter device 10 having two discrete reservoir chambers. For example, it is contemplated in accordance with a preferred embodiment of the present invention that the first and second tubular chambers 12, 14 are welded together, although other coupling techniques maybe utilized in accordance with the present invention.

Needle access to the present implantable catheter device 10, and particularly, the first and second tubular chambers 12, 14, is provided by respective single axial slots 26 within the outer cylinders 18. Since the first and second tubular chambers 12, 14 are substantially identical, the following discussion concerning the construction of the tubular chambers will focus upon the first tubular chamber 12 as shown in detail in FIGS. 11 to 16. Those skilled in the art will readily appreciate the relevance of this discussion in disclosing the construction of the second tubular chamber 14.

Figure 16:
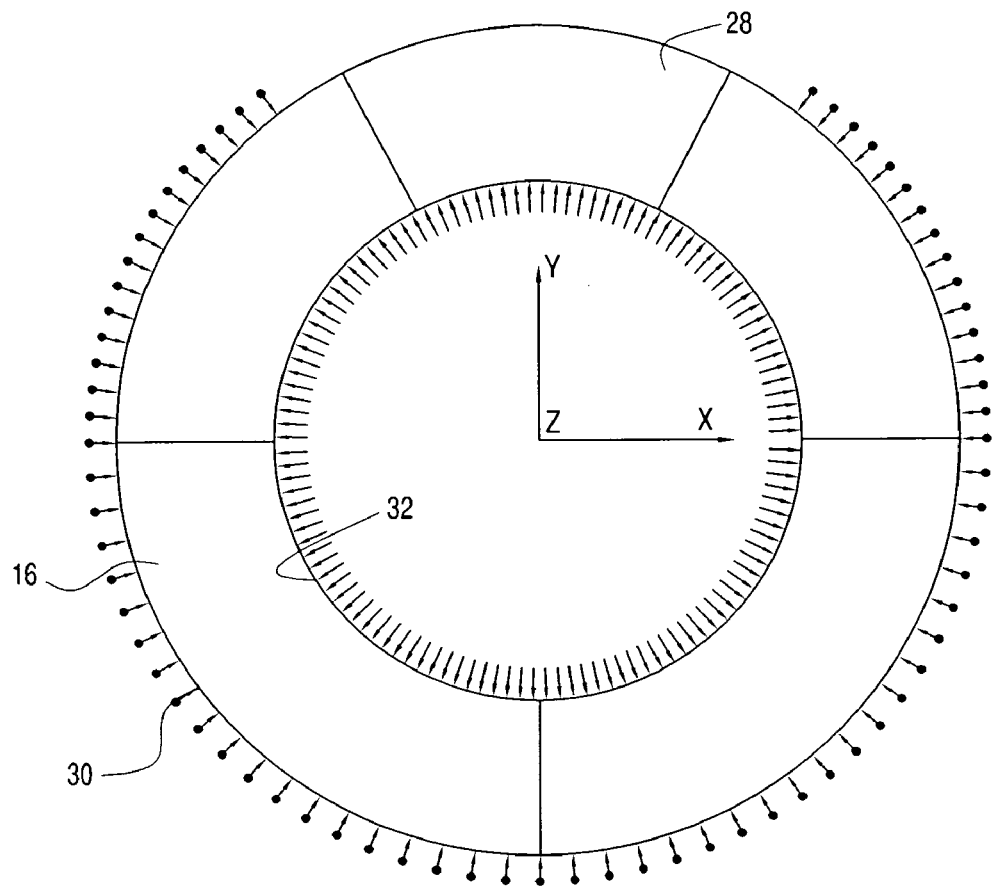
FIG. 16 is an end view of the elastomeric cylindrical member showing applied forces.

As will be discussed in greater detail below, the elastomeric cylindrical member 16 held within the outer cylinder 18 is retained under radial compressive stresses. With reference to FIG. 16, the radial compression applied to the elastomeric cylindrical member 16 provides compressive circumferential hoop stresses in the elastomeric cylindrical member 16. The compressive hoop stresses serve to seal needle holes in the elastomeric cylindrical member 16 following needle withdrawal. Thus, multiple punctures of the elastomeric cylindrical member 16 in the area located adjacent the axial slot 26, that is, the bulge portion 28 formed within the slot 26 of the outer cylinder 18, are sealed during the service life of the catheter device by the compressive hoop stresses applied to the elastomeric cylindrical member 16.

Since the implantable catheter device 10 is constructed with the elastomeric cylindrical member 16 held under stress within the outer cylinder 18, needle access is provided via the axial slot 26 formed in the outer cylinder 18. Radial compression is applied to the elastomeric cylindrical member 16 by the outer cylinder 18, resulting in the self-sealing of the punctured elastomeric cylindrical member 16 as needles are withdrawn. Radial compression is achieved by forming the elastomeric cylindrical member 16 slightly larger than the space into which it fits within the outer cylinder 18.

The present implantable catheter device 10 provides temporary to long term hemodialysis access with fewer long and short term complications when compared to prior art strategies. The present implantable catheter device 10 generally includes a subcutaneously placed, dual chambered device which, when mated to currently-available catheter tubes, allows hemodialysis utilizing current modalities applied by all hemodialysis departments. The present implantable catheter device 10 also decreases the likelihood of infection, facilitates better patient acceptance due to the fact that no portions of the catheter extend outside the body and lessens the possibility of accidental removal with potentially life-threatening implications.

As briefly discussed above, the elastomeric cylindrical member 16 includes an outer wall 30 and an inner wall 32. The elastomeric cylindrical member 16 is constructed from implantable grade silicone rubber. However, those skilled in the art will appreciate the use of other elastomer(s) soft enough to be penetrated by a needle in accordance with the present invention. While specific materials are disclosed above in accordance with a preferred embodiment of the present invention, those skilled in the art will appreciate the fact that the elastomeric cylindrical member 16 may be composed of other structurally equivalent materials without departing from the spirit of the present invention.

In accordance with a preferred embodiment of the present invention, the elastomeric cylindrical member 16 has a durometer of 60 Shore A, an uncompressed inside diameter of 0.315 inches and an uncompressed outside diameter of 0.500 inches. The overall length of the elastomeric member is 1¼" and the axial length of the closed second end 24 of the elastomer is ¼". While specific dimensions are disclosed above for the construction of a preferred embodiment of the present invention, variations in the dimensions of the elastomeric cylindrical member maybe made without departing from the spirit of the present invention.

With reference to the titanium outer cylinder 18, it is constructed with a hollow tubular geometry and includes an open first end 34 and an open second end 36. The outer cylinder 18 further includes an inner wall 38 and an outer wall 40. While the outer cylinder 18 is formed of titanium in accordance with a preferred embodiment of the present invention, those skilled in the art will appreciate that the cylinder may be formed from other biocompatible materials without departing from the spirit of the present invention.

The inner diameter of the outer cylinder 18 is 0.480 inches and the outer diameter of the outer cylinder 18 is 0.500 inches. As mentioned above, each outer cylinder is provided with an axial slot 26. In accordance with a preferred embodiment of the invention, the axial slot 26 is 0.315 inches wide and provides needle access for diameters up to 7 French (0.092 inches). In addition, the 0.315 inch slot 26 provides needle access to the interior of the catheter after the device has been implanted. The slot 26 also provides a large enough opening through which the exposed portion of the elastomeric cylindrical member 16 can bulge, providing the desired compressive stress distribution in the elastomeric cylindrical member 16 for sealing of needle penetration holes. While specific dimensions are disclosed above for the construction of a preferred embodiment of the present invention, variations in the dimensions of the outer cylinder 18 may be made without departing from the spirit of the present invention.

Figure 17:
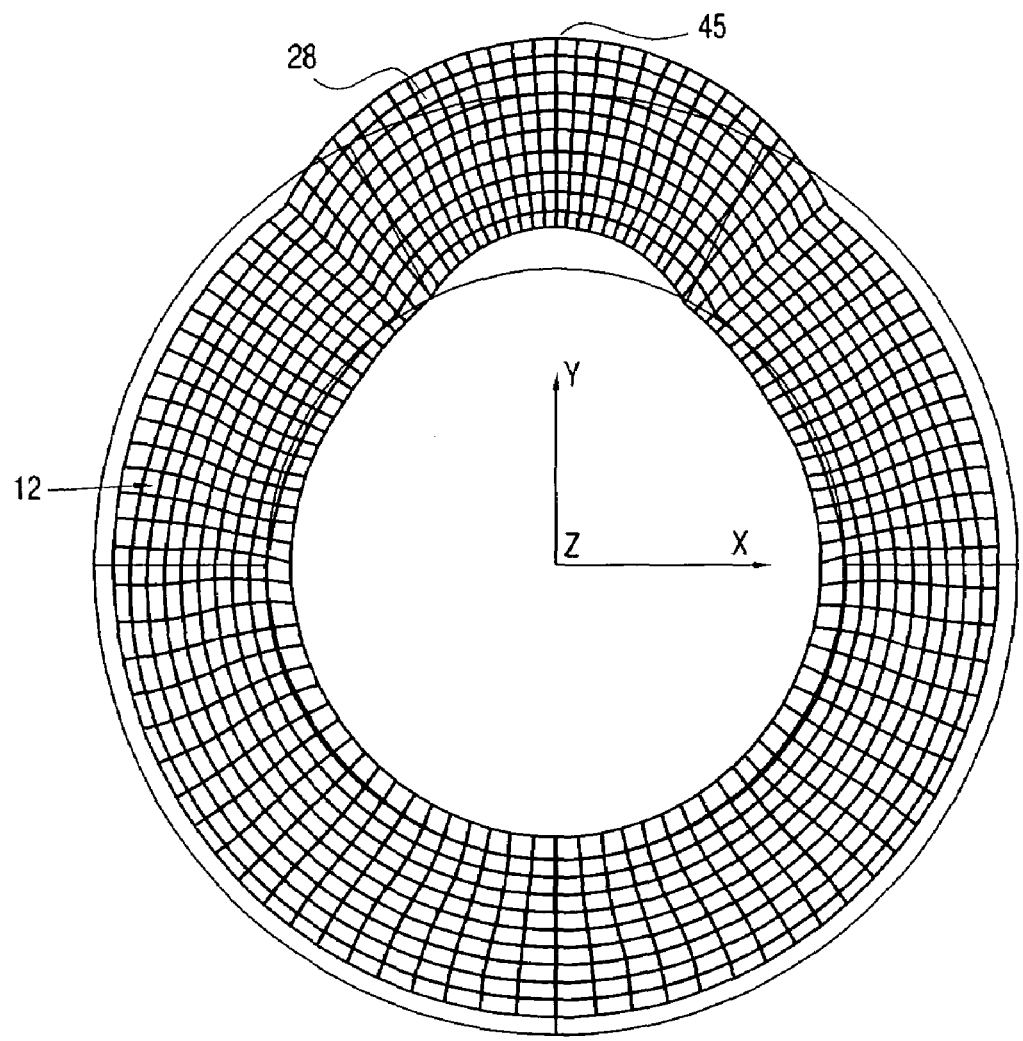
FIGS. 17 and 18 are detailed views of the elastomeric cylindrical member showing deformation thereof based upon various applied forces and constraints.

As mentioned above, the bulge portion 28 of the elastomeric cylindrical member 16 is formed along the axial slot 26 of the outer cylinder 18. The bulge portion 28 is created as a result of the compressive forces under which the elastomeric cylindrical portion 16 is held within the outer cylinder 18. FIG. 17 shows a comparison of the deformed and undeformed geometries of the elastomeric cylindrical member 16 based upon a radial deformation due to the outer cylinder 18 of 0.010" and an internal pressure of 300 mm Hg. Particular attention is directed to the bulging of the elastomeric cylindrical member 16 through the slot 26 in the outer cylinder 18, that is, the bulge portion 28.

Figure 18:
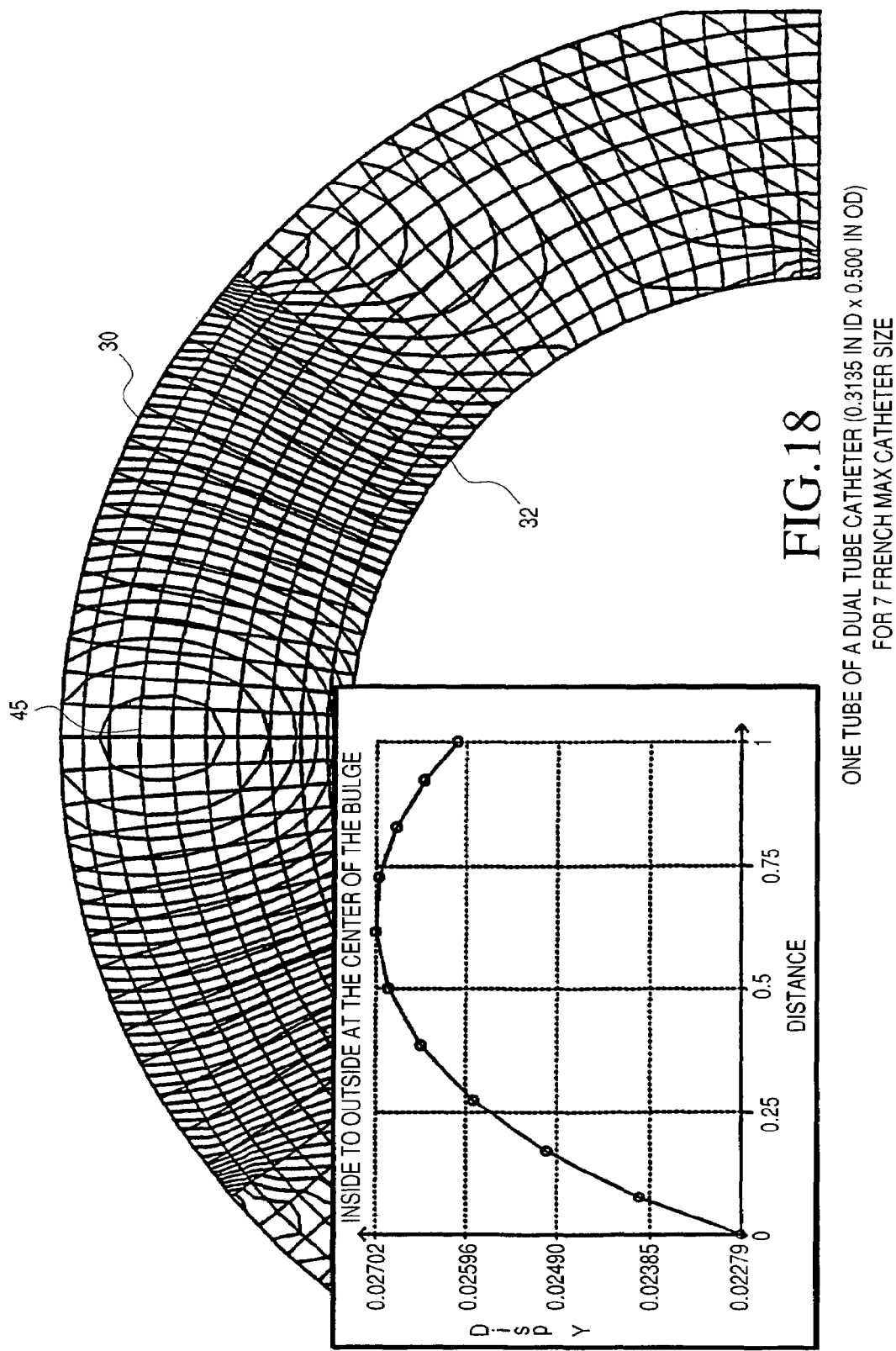

FIG. 18 is a detailed view of the bulge portion 28 of the elastomeric cylindrical member 16. The chart associated with FIG. 18 shows the radial displacement of the centerline 45 of the bulge portion 28 as it protrudes through the slot 26 in the outer cylinder 18. In accordance with a preferred embodiment of the present invention, the inner wall 32 of the elastomeric cylindrical member 16 deflects radially outward by 0.02279" and the outer wall 30 of the elastomeric cylindrical member 16 deflects radially outward by 0.02702". This preferred embodiment is based upon an internal blood pressure of 300 mm Hg and radial compression due to the outer cylinder 18 of 0.010 inches.

Figure 19:
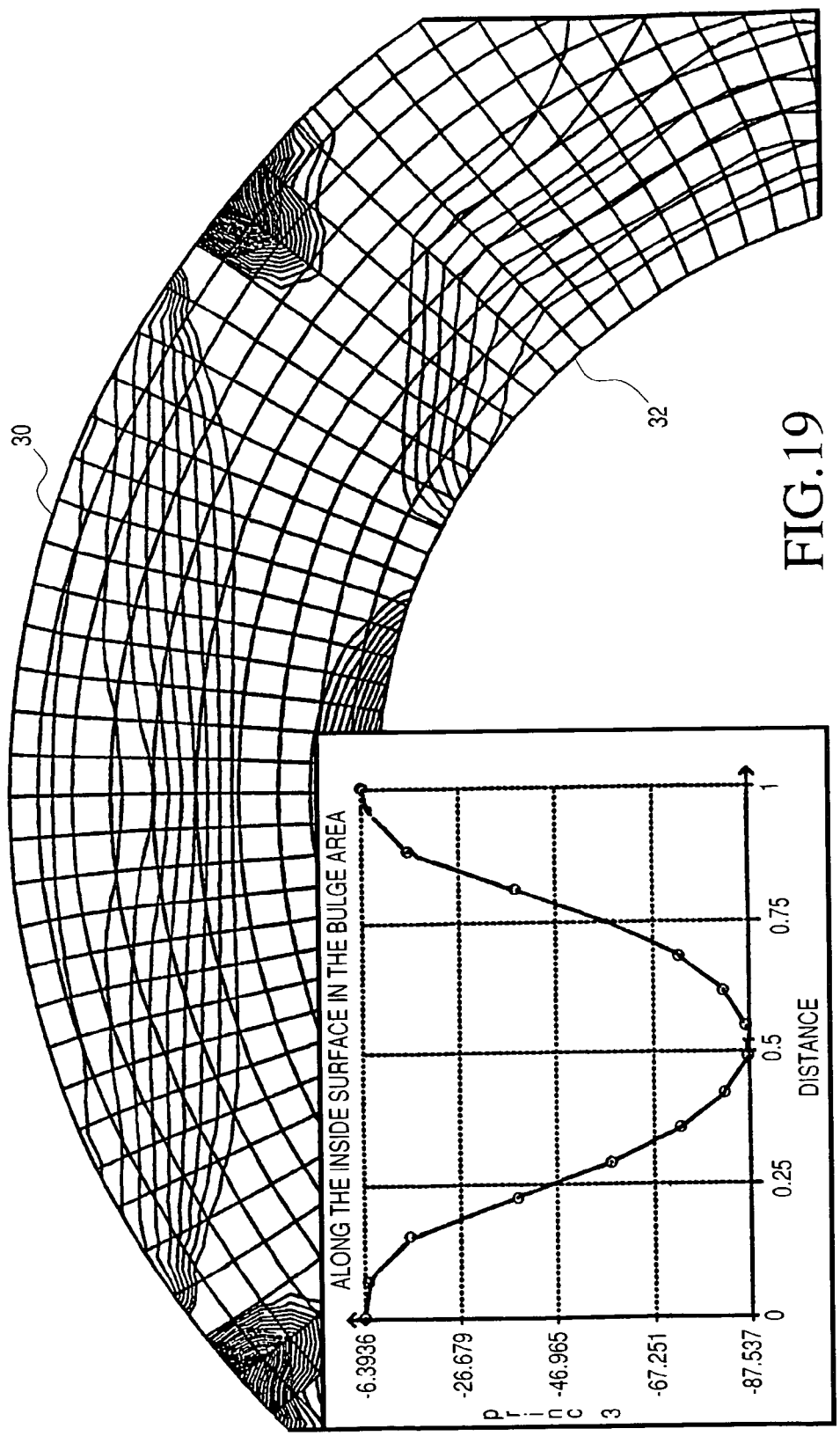
FIGS. 19 to 21 show the minimum principal stresses in various locations within the model.

Further detail of the bulge portion 28 is shown in FIG. 19. Specifically, FIG. 19 shows the inner wall 32 of the elastomeric cylindrical member 16 at the bulge portion 28 as it is subjected to circumferential compressive stress ranging from approximately 6½ to 88 psi. This is believed to be more than adequate for sealing the needle holes in the elastomeric cylindrical member 16 when the elastomer is subjected to an internal pressure of 300 mm Hg. Note that the entire bulge portion 28 is subjected to circumferential compression ranging from 6 psi at the edge of the slot 26 to 87 psi at the centerline 45 of the bulge portion 28.

Figure 20:
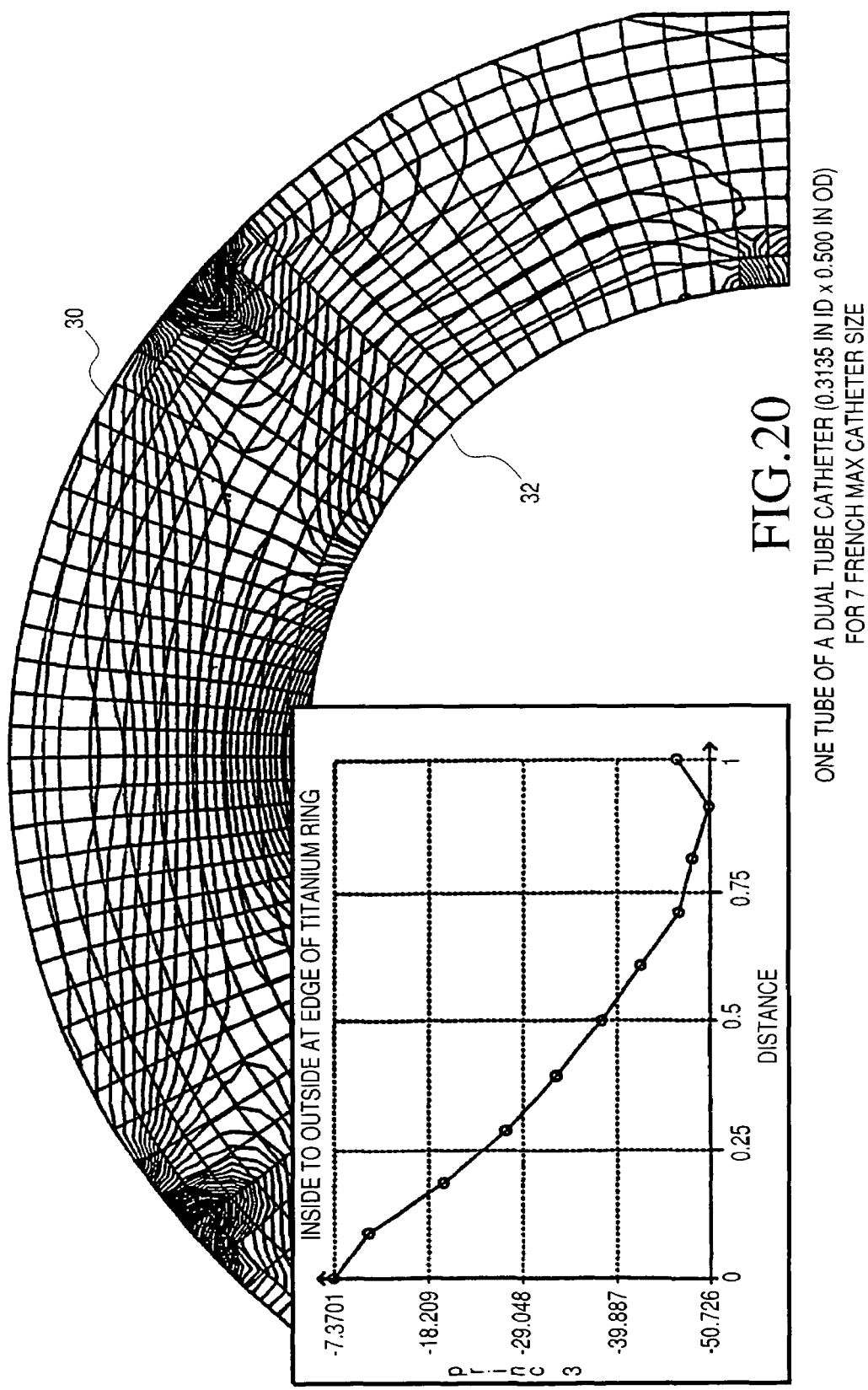

In addition to the detail shown in FIG. 19, FIG. 20 shows the compressive circumferential stress in the elastomeric cylindrical member 16 at the edge of the slot 26 in the outer cylinder 18. The chart on FIG. 20 shows a compressive stress variation in the bulge portion 28 of the elastomeric cylindrical member 16 of approximately 7 to 51 psi at the edge of the slot 26 of the outer cylinder 18.

Figure 21:
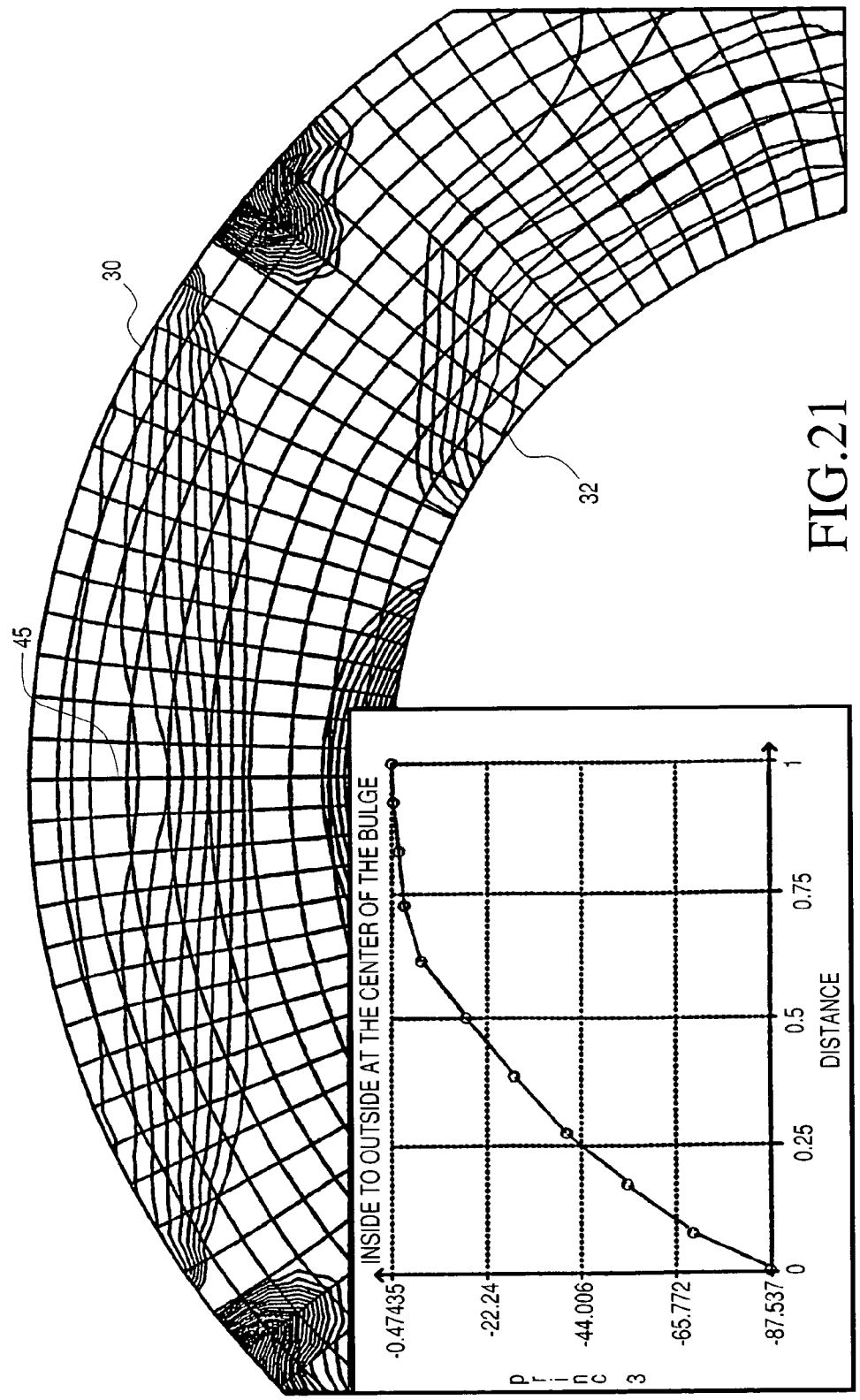

FIG. 21 shows the compressive circumferential stress along the centerline 45 in the bulge portion 28. The graph of FIG. 21 shows a compressive stress variation up to 87 psi at the centerline 45 of the bulge portion 28. In general, FIGS. 20 and 21 show that the entire radial section anywhere in the bulge portion 28 is under circumferential compression, thus ensuring that all needle penetration holes will be sealed after removal of the needle. The high compressive stress levels further ensure closing of the needle penetration holes after repetitive punctures.

In fact, and as will be discussed in greater detail below, the bulge portion 28 is commonly punctured by needles as access to the implantable catheter device 10 is required. With this in mind, FIG. 22 shows a half section of the bulge portion 28 in the elastomeric cylindrical member 16 about to be penetrated by a pointed object 44 with a diameter of about 7 French. FIG. 23 shows the deformation in the elastomeric cylindrical member 16 after it is penetrated by an object 44 with a 7 French diameter. FIG. 24 shows the high stress level developed in the elastomeric cylindrical member 16 at full penetration of the 7 French device 44. The compressive stresses resulting upon puncture as shown above, are indicative of a system which will self-seal upon removal of the penetrating needle 44.

Figure 25:
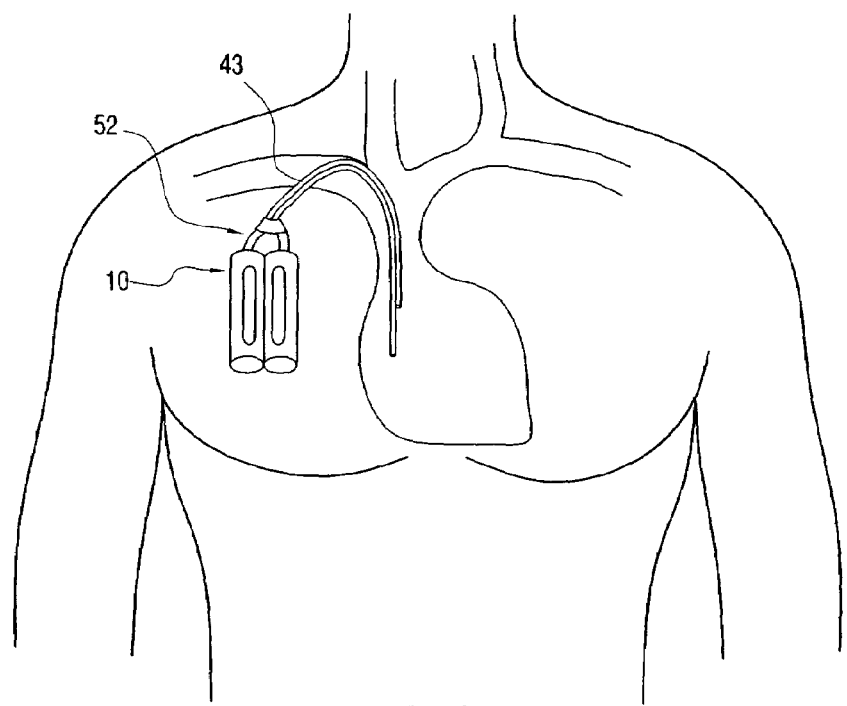
FIG. 25 is a schematic showing implantation of the present implantable catheter device.
Figure 26:
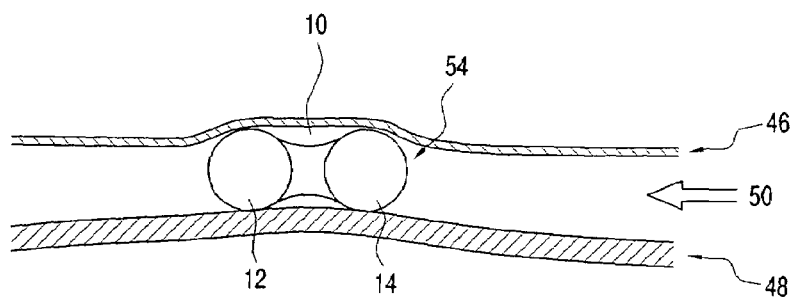
FIG. 26 is a cross section view showing the catheter device positioned with a subcutaneous pouch.

Use of the implantable catheter device is now described with reference to FIGS. 25 and 26, the implantable catheter device 10 is located in a selective region, the catheter tubes 43 are coupled to the respective end cap 22 of the first and second tubular chambers 12, 14 using conventional techniques. For example, the ends of the catheter tubes 43 are attached to the implantable catheter device 10 via the screw threads 42 formed on the end cap 22. The subcutaneous implantable catheter device 10 is then accessed via needle punctures.

More particularly, the catheters 43 used in coupling the implantable catheter device 10 to the vascular system are placed into the venous system exactly as other currently available hemodialysis catheters are positioned. Instead of the catheters simply exiting the vessels and lying draped over the skin surface 46, the catheters 43 are connected to the present implantable catheter device 10 positioned between the skin surface 46 and the muscle 48 within the subcutaneous tissue 50, much like a permanent pacemaker is implanted subcutaneously. By placing the implantable catheter device 10 subcutaneously, the potential for infection and undesirable contact is minimized.

Once implanted, the implantable catheter device 10 is ready for hemodialysis by accessing the bulge portion 28 with a 15 gauge needle, or other sizes, exactly as if it were a conventional catheter or surgically created fistula. By palpating and locating the entry sites in the present device 10, the implantable catheter device 10 is easily accessed. As those skilled in the art will readily appreciate, one chamber of the implantable catheter device 10 functions as the arterial chamber, which is connected to the arterial catheter limb and the other chamber functions as the venous chamber, which is connected to the venous catheter limb. As those skilled in the art will certainly appreciate, the system of using one line for arterial hemodialysis and one for venous hemodialysis is currently practiced for both fistula and catheter hemodialysis in the prior art. After a hemodialysis session is terminated, the needles are simply removed and pressure is held over the implant site in the same manner as if one were accessing a surgically created fistula.

Flow rates significantly greater than the standard rates used for hemodialysis (500 cc/min) are easily accommodated by the present implantable catheter device 10. The unique design of the present implantable catheter device 10 generally is composed of a dual chambered elastomeric device enclosed in a titanium shell of slightly smaller diameter.

In summary, the elastomeric cylindrical member 16 and the outer cylinder 18 are designed to produce stresses in the dual chambered device automatically sealing the needle puncture sites when the needle 44 is removed. The seal is effective over a substantial time period and repeated puncturing of the device does not affect its sealing ability. The seal is created as a result of the bulge portion 28 generated by the compression of the elastomeric cylindrical member within the outer cylinder. This bulge portion 28 may also be used to locate the needle puncture site by palpation.

With regard to the placement of the present device 10 within a patient, standard aseptic techniques are strictly observed. The internal jugular vein is cannulated, preferably by a 20 gauge needle or smaller, and a guidewire is placed through the needle and into the SVC (superior vena cava). The needle is removed, and a peel-away sheath is placed over the wire and into the SVC. A suitable subcutaneous site is located in the upper chest 52, and the area is anaesthetized utilizing local anaesthetic. A scalpel is used to make a skin incision of several centimeters length, and blunt dissection of the underlying subcutaneous tissues 50 is performed to create a "pouch" 54 in which to place the present dual chamber, implantable catheter device 10. The track below the skin surface 46 between the "pouch" 54 and the heretofore mentioned sheath in the SVC is anaesthetized by local anaesthetic. The two components, being the present catheter device 10 and the standard PTFE catheters 43 are connected once removed from the kit. The end tip, or end, of the catheter 43 not connected to the present implantable catheter device 10 is attached to a "tunneling device", of which many are currently available in the prior art. The tunneling device is entered from the "pouch", and steered toward the other skin opening, that is, the area where the sheath exits the skin 46. The end of the tunneling device is pulled through the skin opening adjacent the sheath and the end of the catheter 43 is subsequently pulled through the tunnel track. The introducer is removed from the sheath, and the end of the catheter 43 is fed into the peel-away sheath, and into the SVC The small skin opening at this site can now be sutured. The proximal end of the catheter 43 attached to the present implantable catheter device 10 is now properly adjusted in the subcutaneous "pouch" 54. The skin wound adjacent to the implantable catheter device 10 is now approximated by suture. The present device 10 is now ready to be accessed, and by piercing the skin 46, the device 10 is accessed, blood is aspirated, then subsequently forward flushed utilizing heparinized saline. The skin sutures can be removed, as is routine, in 7–10 days. The implantable catheter device 10 is now ready for hemodialysis.

If replacement of the implantable catheter device 10 becomes necessary, a skin 46 incision is placed adjacent to the present implantable catheter device 10. Blunt dissection is performed to loosen the device 10 from the surrounding tissues 48, 50. The implantable catheter device 10, and attached catheter 43, are simply withdrawn several centimeters and the implantable catheter device 10 is detached from the catheter 43. Through the end of the catheter 43, a guidewire is placed into the SVC. The old catheter is removed and, in a similar fashion, a "new" catheter is advanced over the existing guidewire and into the SVC The guidewire is removed, and the end of the catheter 43 attached to a "new" implantable catheter device 10. The unit is advanced a final centimeter or so and properly seated into the subcutaneous "pouch" 54. Again the skin 46 is approximated by suturing.

Testing & Analysis

In an effort better understand the efficacy of the present invention, testing and analysis of the present invention were performed.

For testing purposes, a non-implantable silicone tubing manufactured by Saint Gobian Performance Plastics was used as the elastomeric cylindrical member. Since the physical properties of the implantable and non-implantable materials are the same, the test results should be equivalent. In addition, the open end of the silicone tubing was closed using solid, stainless steel plugs.

Testing was conducted using water instead of blood. Hydrostatic pressure was applied to the catheter by means of translucent silicone tubing as described herein. Essentially, the testing consisted of setting the desired hydrostatic pressure head on the catheter, puncturing the silicone tubing with a 16 Ga needle and checking for leakage from the silicone tubing as the pressure head was maintained. The details are discussed in detail in the attached Appendix. As one can see, the tested prototype maintained a "no leakage" condition after 312 punctures with a 16 Ga needle under a pressure head of 4.87 psi. This corresponds to a dialysis schedule of three times a week for a period of two years.

I then conducted an investigation to determine the "no leakage" pressure attainable as the number of punctures was increased substantially. The results of this investigation show that, for the prototype tested with silicone tubing having an OD/ID of 0.5/0.3125 inches, a "no leakage" condition of 13 mm Hg was maintained after 950 punctures with a 16 Ga needle.

The primary function of the silicone tubing is to maintain a "no leakage" condition which meets the requirements of the patients constraints. The area of the silicone tubing which is available for puncturing and the overall geometry which may be tolerated by the patient are the important parameters. The area of the silicone tubing available for puncturing is a function of the length of the slot in the metallic outer cylinders and the outer diameter of the silicone tubing. After the overall geometry of the catheter has been established by the designer to meet the patients constraints, the silicone tubing area available for puncturing can be maximized using the Prototype Scaling equations as found in the attached Appendix.

The "Implantable Catheter Puncture Analysis" and "Prototypes Scaling" sections found in the attached Appendix maybe used by those skilled in the art to maximize the silicone tubing area available for puncturing. The objective is to obtain the largest number of single punctures possible based on the geometry constraints.

As an example of the use of the scaling analysis, the parameters of the tested prototype were substituted in the scaling equations. The maximum number of 16 Ga single punctures calculated was P=68. This means that, theoretically, puncture number 69 goes through an existing hole in the silicone tubing. It should be noted at this point that the silicone tubing sealed completely in the tested prototypes after tolerating hundreds of punctures more than the 68 calculated. This is due to the compressive stresses developed in the silicone tubing as predicted by finite element analysis and is the basis for the present invention. Testing of the present prototype showed that 950 punctures with a 16 Ga needle were sealed with a catheter pressure of 13 mm Hg. For 312 punctures, the catheter sealing pressure was 4.87 psi (252 mm Hg). We have, therefore, a means of plotting the number of punctures that can be satisfactorily sealed at all the sealing pressures.

In accordance with a second example, one may assume that more than 950 punctures were made in silicone tubing compressed in accordance with the present invention. One might choose to increase the length of the slot and thereby increase the number of single punctures. Referring to calculations found in the attached Appendix, one sees that by increasing the length of the slot by ¼ inch, the number of single puncture is calculated to increase from 68 to 93. If the required sealing pressure is 13 mm Hg, the number of punctures expected in accordance with the present compressed silicone tubing would be approximately 37% more than the 950 punctures, that is, 1300 punctures. It is believed that testing of a new prototype with a ¼ inch longer slot would also let us plot the number of punctures against sealing pressure so that we could determine the increase in sealing pressure achievable at 950 punctures.

In accordance with a further example, one may increase the outer diameter of the silicone tubing to ⅝ inch and calculate the number of single punctures. Referring to the calculations found in the attached Appendix, the number of punctures is calculated to increase from 68 to 118. If the sealing pressure is 13 mm Hg, the expected number of punctures in accordance with the present compressed silicone tubing would, therefore, be increased from 950 to 1634 by such a thickness increase.

Figure 27:
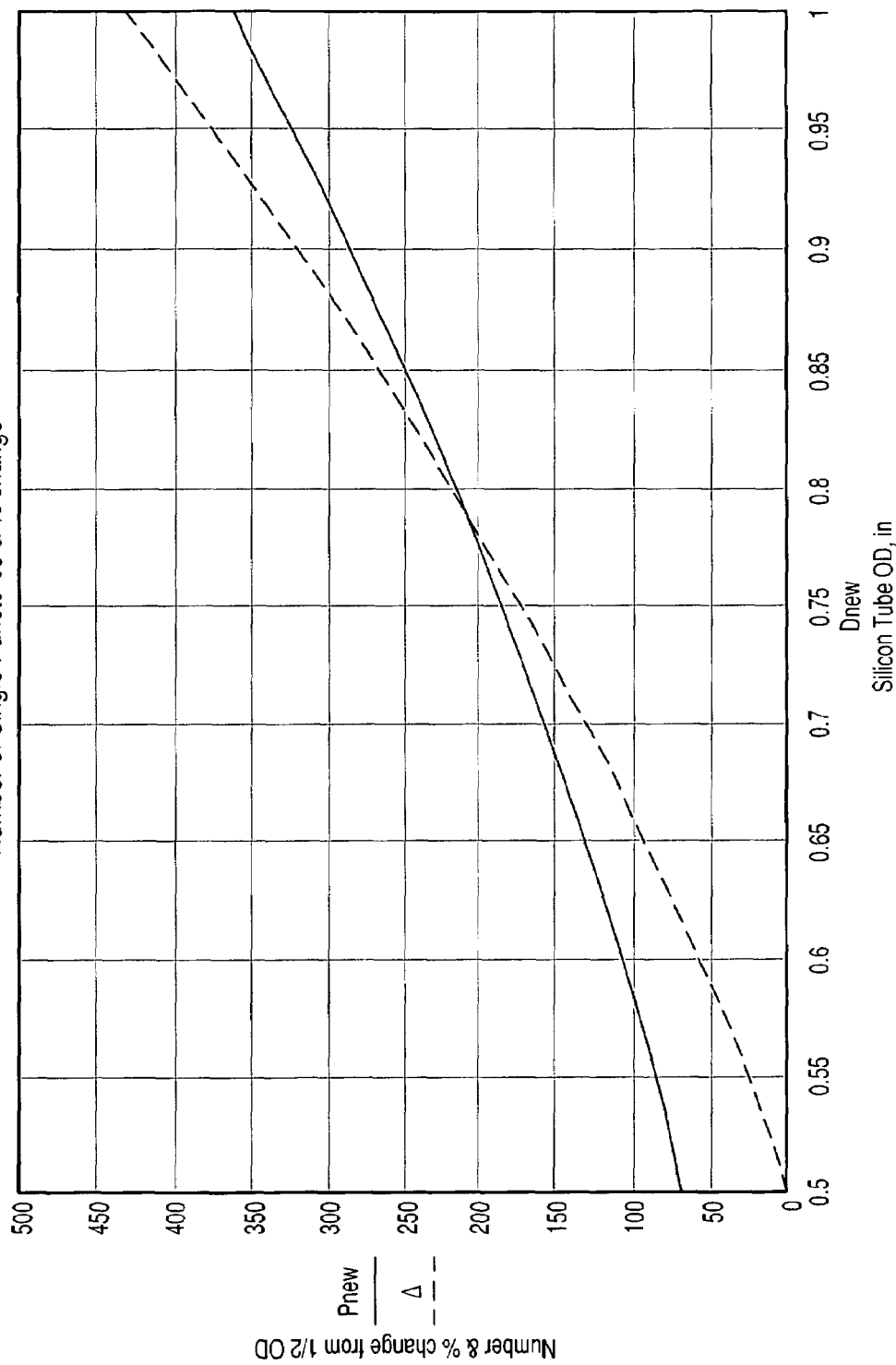
FIG. 27 is a chart showing the number of single punctures and the percentage change from the prototype with ½ inch OD silicone tubing as a function of the outer diameter of the silicone tubing.

FIG. 27 is a chart showing the number of single punctures and the percentage change from the prototype with ½ inch outer diameter silicone tubing as a function of the outer diameter of the silicone tubing. For silicone tubing and other diameters from ½ to 1 inch, the percentage increase can be determined from the chart.

Figure 28:
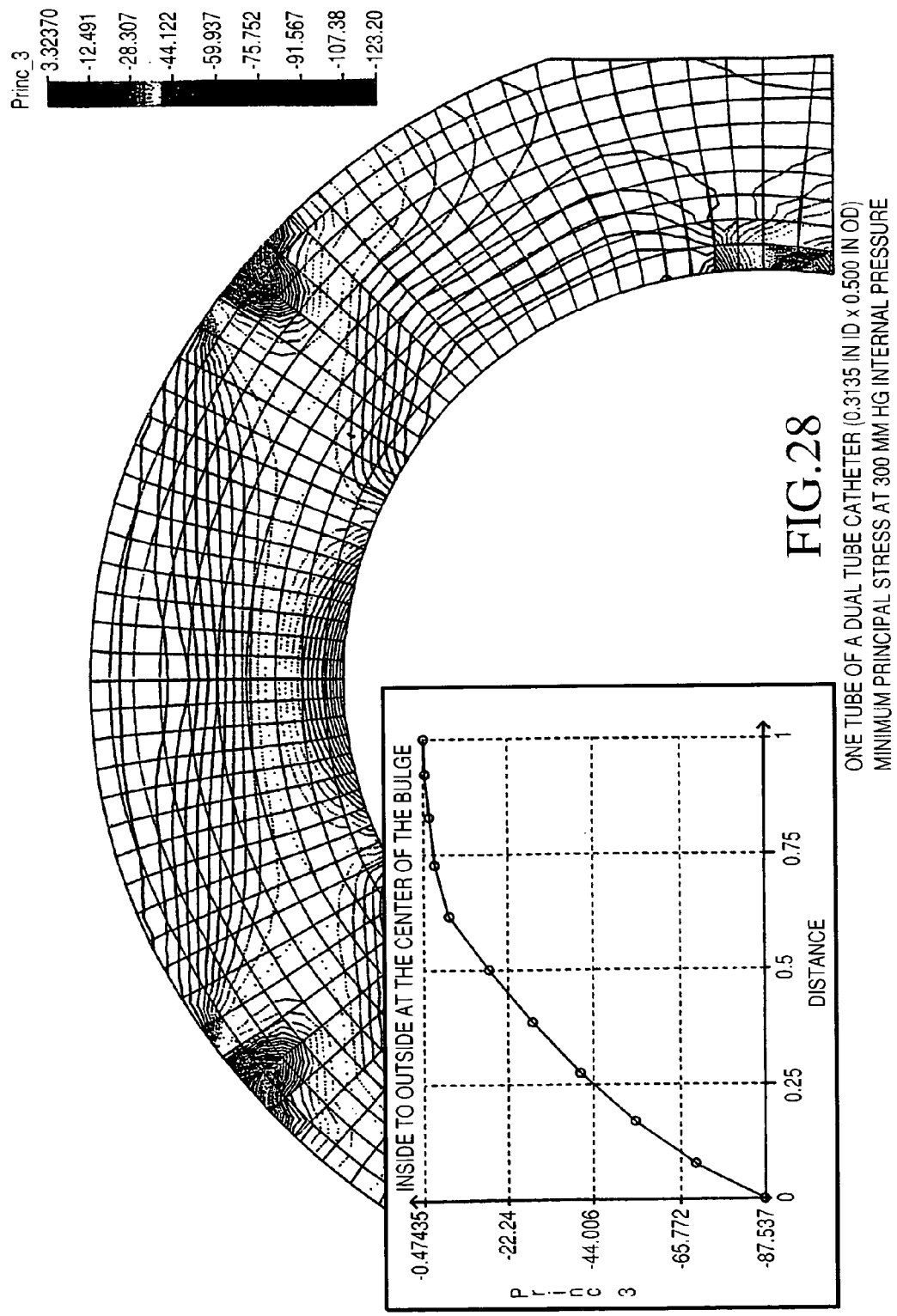
FIGS. 28 and 29 show finite element analysis of the tubing in accordance with the present invention.
Figure 29:
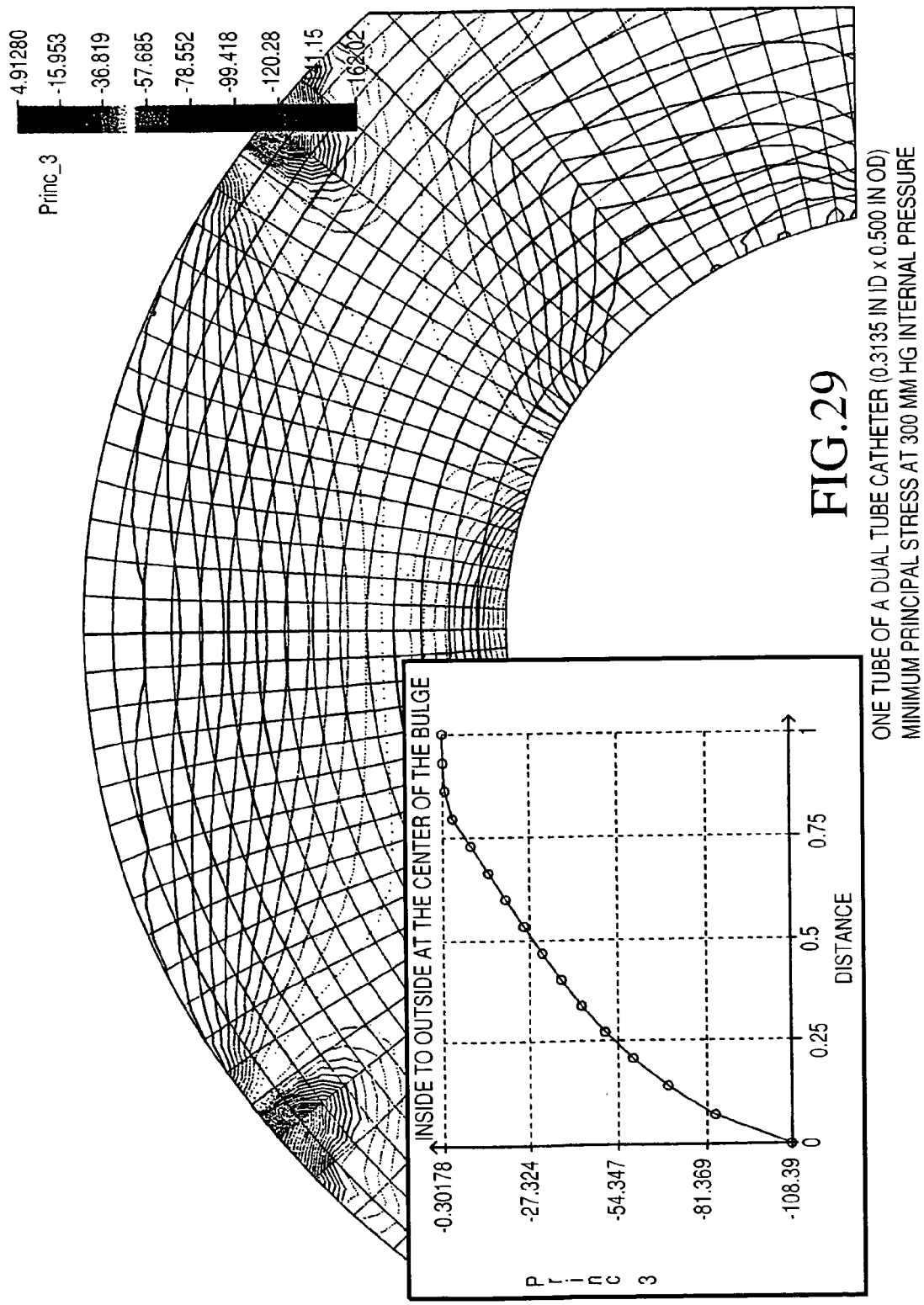

In accordance with a further embodiment, and with reference to a Finite Element Analysis found in FIGS. 28 and 29, a minimal principal stress distribution in the center of the bulge is shown. This is the center of the region which is accessible for puncturing of the silicone. The plot shown in FIG. 28 is for a silicone outer diameter of ½ inch and an inner diameter of 5/16 inch. The second plot shown in FIG. 29 is for a silicone tubing having an outer diameter of ½ inch and an inner diameter of ¼ inch. The thickness of the silicone wall in the first case is 0.09375 inches and in the second case is 0.125 inches. Note on the graph that the minimal principal stress (princ 3) increases as the wall thickness increases. The minimum principles stress for 0.09375 inch wall thickness is −88. For the 0.125 inch wall thickness, the minimum principal stress is −108 psi. Hence, in addition to the modeling changes described above, the silicone sealing pressure can also be increased by increasing the wall thickness of the silicone tubing independently of the other modeling changes.

While the preferred embodiments have been shown and described, it will be understood that there is no intent to limit the invention by such disclosure, but rather, is intended to cover all modifications and alternate constructions falling within the spirit and scope of the invention.

APPENDIX

Implantable Catheter Summary

A mathematical analysis of the Implantable Catheter was conducted to determine the relationship between selected parameters of the Dialysis machine, the needle and the silicone tubing portion of the Implantable Catheter.

The analysis is based on the following :

1) 16 Gauge needle geometry

2) Dialysis machine flow rates of 300 and 400 cc/min

3) Dialysis machine pressures at the needle input of 160 and 180 mm Hg

4) Mean blood density of 0.0383 #/in^3

5) Needle OD / silicone tubing friction coefficient = 0.4

6) Mean compressive stress at the needle OD / silicone tube interface = 1000 psi The values of the friction coefficient and the mean compressive stress are typical values and may be changed to suit the actual conditions. The mean compressive stress may be calculated using Finite Element Analysis techniques. The details of the analysis are included in the appendix. The results are summarized below :

| Q cc/min | pd mm Hg | min pn mm Hg | min pc mm Hg |
|---|---|---|---|
| 300 | 160 | 120 | 160 |
| 400 | 160 | 90 | 160 |
| 300 | 180 | 141 | 180 |
| 400 | 180 | 111 | 180 |

Where:

Q = flow rate from the Dialysis machine pd = pressure at the needle input from the Dialysis machine min pn = minimum pressure in the needle min pc = minimum pressure in the catheter Referring to the graphs of needle and catheter pressures in the appendix, we see an increase in needle and catheter pressures for tubing inlet ID's below 0.19 inches. For tubing inlet ID's greater than 0.19 inches, the needle and catheter pressures are essentially constant and the catheter pressure is equal to that at the needle input from the Dialysis machine. Hence, to achieve the lowest possible pressure in the catheter, the tubing inlet ID from the Dialysis machine should be 0.19 inches or larger.

Testing

A prototype of the Implantable Catheter was fabricated in accordance with the teachings of Provisional Patent docket # MILLoo1 issued to Stuart Henry Miller. For non - implant test purposes, the metallic portions of the device were fabricated from stainless steel. The silicone tubing was SANITECH 50 part # STHT-C-312-3 with lot # C09206 manufactured by Saint Gobain Performance Plastics. The certificate of conformance is included in the appendix.

The prototype was tested for leakage from the silicone tubing following multiple punctures with a 16 gauge needle. The punctures were made at approximately 90 degrees to the longitudinal axis of the silicone tubing.

The catheter was prepared for testing by attaching a suitable length of flexible tubing to the fittings at the end of the catheter. The tubing varied in length from 36 to 150 inches. The tubing and catheter were then filled with water from the open end of the tubing. When the water level completely filled the catheter, the open end of the catheter was closed by inserting the stainless steel end cap. This procedure was used to prevent trapping air in the device.

For the initial testing, the catheter was placed on a flat surface so that the longitudinal axis of the silicone tube was horizontal. The open end of the water filled tubing was then raised until a 3 inch pressure head was produced in the catheter. The silicone tubing was then punctured using a 16 gauge needle. The needle was withdrawn and the silicone tubing was inspected visually for leakage at the puncture site. No leakage was observed. The water level in the tubing was then marked and checked periodically for 24 hours.

No leakage was observed after 24 hours with a 3 inch water head. The puncture site remained dry.

The testing was then continued by puncturing the silicone tubing repeatedly with the 16 gauge needle for a total of 156 times which corresponds to a Dialysis schedule of three times a week for one year. No leakage was observed after 156 punctures with a three inch water head.

The punctured silicone tubes were then removed and replaced with fresh tubes and the testing was continued with increased pressure loads on the catheter. The pressure was increased by raising the open end of the flexible tubing incrementally to produce a pressure head of 135 inches of water. This corresponds to a pressure of 4.87 psi ( 252 mm Hg) in the punctured silicone tubing. Again, no leakage was observed at the puncture site after 156 punctures when the silicone tubing was subjected to a water head of 135 inches ( 252 mm Hg ).

The silicone tube was then punctured an additional 156 times for a total of 312 punctures. No leakage was observed after 312 punctures which corresponds to a Dialysis schedule of three times a week for two years. The punctured silicone tubing was then replaced with fresh samples and the test was repeated at a pressure loading of 135 inches of water. No leakage was observed.

Conclusion

Preliminary testing indicates that the Implantable Catheter will seal after multiple punctures with a 16 gauge needle equivalent to 1 to 2 years of Dialysis with a three times per week schedule.

Recommendations

The testing should be repeated using implantable grades of silicone tubing and either titanium or other suitable implantable materials for the structural portions of the Implantable Catheter. The preliminary testing was conducted at room temperature. It is therefore recommended that testing be conducted at temperatures encountered at the implantation site. Animal studies should be conducted to evaluate the overall performance of the implantable catheter prior to testing in humans.

hfm
10/23/01

IMPLANTABLE CATHETER FLUID FLOW

HFM 8/20/01

| | |
|---|---|
| $w := .0383$ | Blood density,#/in^3 (see Physics by Kane & Sternheim pg 271) |
| $g := 386.4$ | accel due to gravity,in/sec^2 |
| $D := .064$ | OD of the needle |
| $dd := .056$ | ID of the tubing from the Dialysis machine to the needle,in |
| $dn := .056$ | ID of the needle,in |
| $dc := .3125$ | ID of the catheter,in |
| $Q := .305$ | Flow rate of the blood,in^3/sec (in^3/sec = .061023*cc/sec)) |
| $pd := 3.09$ | pressure at the inlet to the needle,psi (1mm Hg *.01934 = psi) |
| $\mu := .4$ | Friction coeff needle/catheter tubing |
| $\sigma := 1000$ | mean compressive stress on the needle,psi |

Mass density of the blood, #sec^2/in^4

$$\rho := \frac{w}{g}$$

Cross sectional areas, in^2

$$Ad := \frac{\pi \cdot dd^2}{4} \qquad An := \frac{\pi \cdot dn^2}{4} \qquad Ac := \frac{\pi \cdot dc^2}{4}$$

Flow Velocities, in/sec $$Vd := \frac{Q}{Ad} \qquad Vn := \frac{Q}{An} \qquad Vc := \frac{Q}{Ac}$$

Pressures, psi $$pn := pd + \frac{\rho \cdot Q^2}{2}\left(\frac{1}{Ad^2} - \frac{1}{An^2}\right) \qquad \text{in the needle, psi}$$

$$pc := pd + \frac{\rho \cdot Q^2}{2}\left(\frac{1}{Ad^2} - \frac{1}{Ac^2}\right) \qquad \text{in the catheter, psi}$$

Mass flow rate, #sec/in $$m := \rho \cdot Ad \cdot Vd \qquad \text{constant}$$

Axial forces on the needle due to momentum change in the blood, Fm $$Fm := pn \cdot An - pc \cdot Ac + m \cdot Q \cdot \left(\frac{1}{An} - \frac{1}{Ac}\right)$$

due to friction between needle & catheter tubing, Ff $$Ff := \mu \cdot \pi \cdot \left(\frac{.5 - .3125}{2}\right) \cdot \sigma \cdot D \qquad \text{for a .5 ODx.3125 ID silicone tubing}$$

due to static pressure, pc, on the needle, Fs $$Fs := \frac{pc \cdot \pi \cdot D^2}{4}$$

Ftotal := −Fs + Fm + Ff      Ftotal must be positive to keep needle in silicone tubing

Results $m = 3.023 \times 10^{-5}$      #sec/in $\rho = 9.912 \times 10^{-5}$      #sec^2/in^4

$Ad = 2.463 \times 10^{-3}$      $An = 2.463 \times 10^{-3}$      $Ac = 0.077$      in^2

$Vd = 123.832$      $Vn = 123.832$      $Vc = 3.977$      $\frac{in}{sec}$ $pn = 3.09$      $pc = 3.849$      psi $Fm = -0.284$ #     $Ff = 7.54$  #/σ=1000     $Fs = 0.012$ #     $Ftotal = 7.243$  #/σ=1000

Note: A negative pressure in the needle indicates a cavitation condition in the needle for the values of the parameters given. The negative pressure may be avioded by increasing the value of the pd term and/or reducing the value of the second term in the equation by making Ad closer to the value of An. If Ad = An, the second term in the equation drops out and we have pn = pd.

Let's plot the pressure in the needle as a function of Ad
$$Ad(dd) := \frac{\pi \cdot dd^2}{4}$$
$$dd := .0025, .005 \ldots .32$$
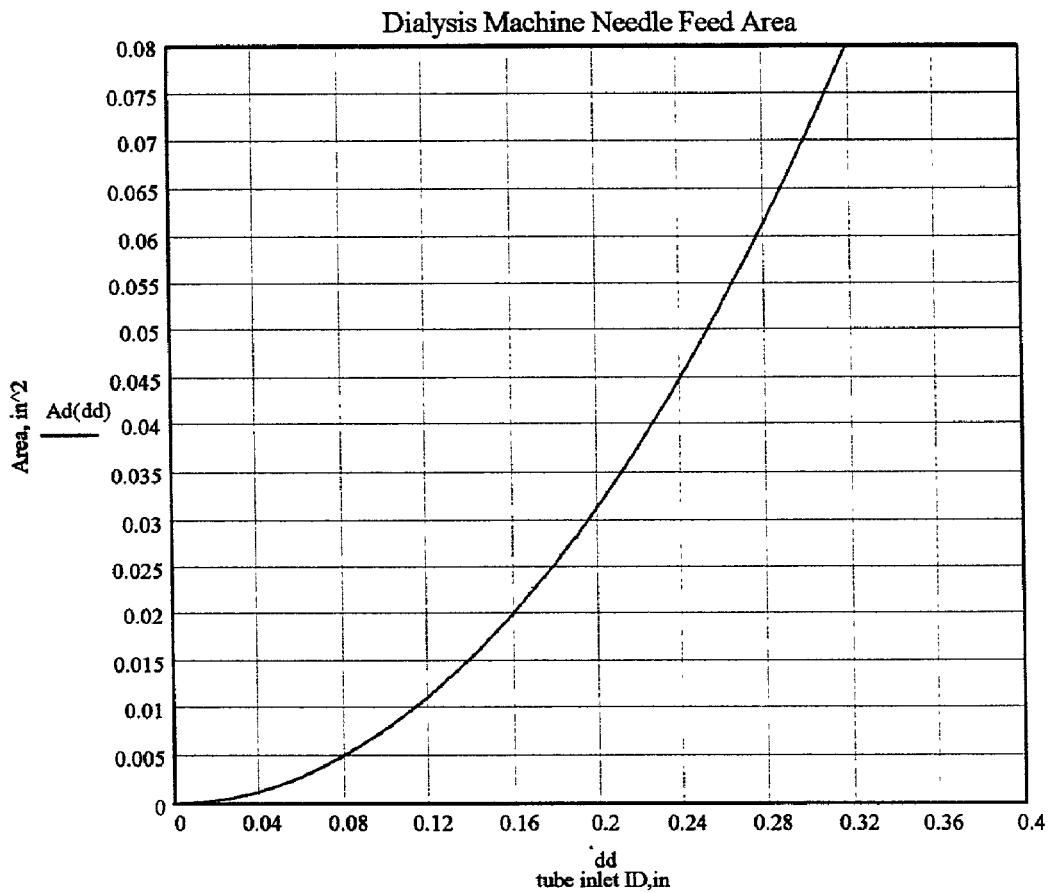
$$pn(dd) := pd + \frac{\rho \cdot Q^2}{2} \cdot \left( \frac{16}{\pi^2 \cdot dd^4} - \frac{1}{An^2} \right)$$
$$dd := .056, .057 \ldots .32$$

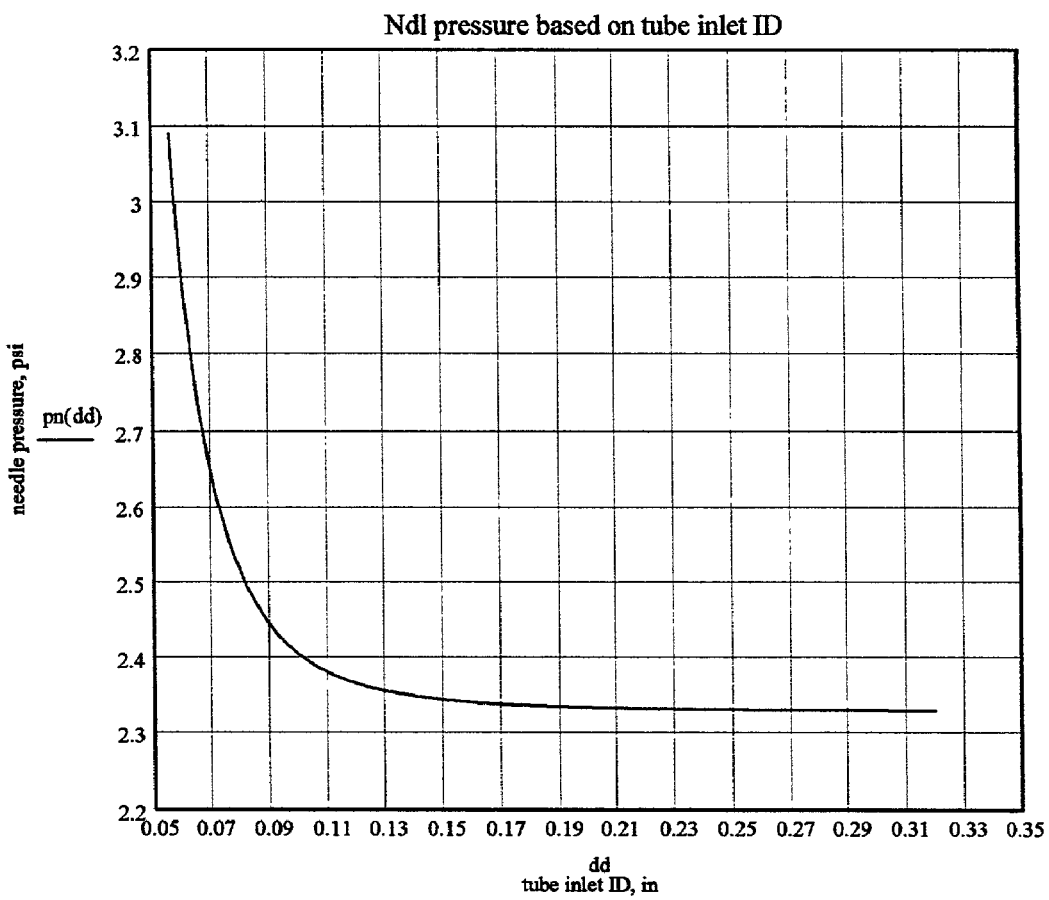
Let's plot the catheter pressure, pc, as a function of the ID of the tubing from the Dialysis machine
$$pc(dd) := pd + \frac{\rho \cdot Q^2}{2}\left(\frac{16}{\pi^2 \cdot dd^4} - \frac{1}{Ac^2}\right)$$
$$dd := .056, .057 \ldots .32$$

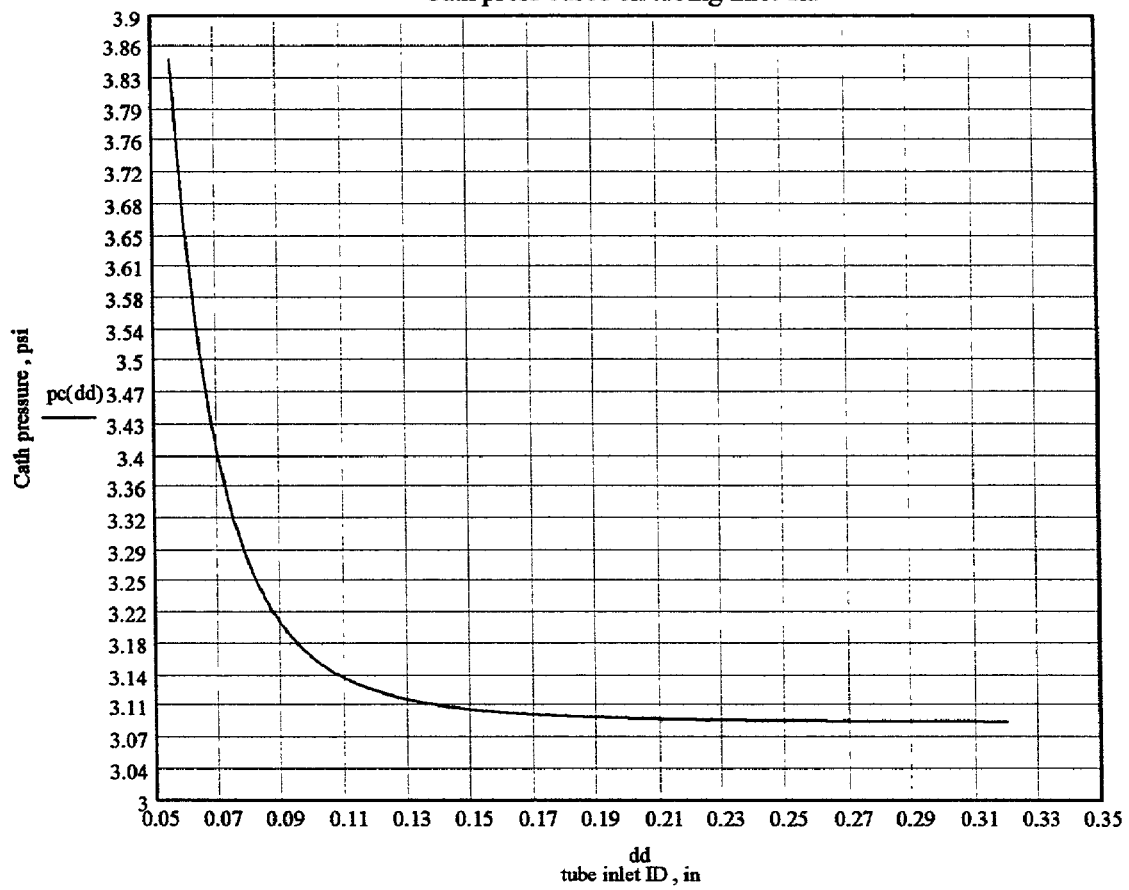

Implantable Catheter Puncture Analysis     HFM 01/18/02

This analysis calculates the maximum number of single punctures that can be made in the silicone tubing without penetration of the same hole a second time.

The parameters required are as follows ( based on the original prototype ):

| | |
|---|---|
| $w := .3115$ | width of the slot, in |
| $L := .4625$ | axial length of the parallel sides of the slot, in |
| $D := 0.500$ | outer diameter of the silicone tubing, in |
| $d := 0.064$ | outer diameter of the needle which punctures the silicone tubing, in ( 16 gauge needle ) |

The required equations are as follows $$A := w \cdot L + \frac{\pi \cdot w^2}{4} \quad \text{max area of the silicone tubing which can be punctured, in}^2$$

$$\alpha := \operatorname{asin}\left(\frac{w}{D}\right) \quad \text{one half of the angle of the slot measured from tubing center, deg}$$

$$a := \frac{\pi \cdot d^2}{4} \quad \text{cross sectional area of the puncture needle, in}^2$$

$$P := \frac{w \cdot (4 \cdot L + \pi \cdot w)}{\pi \cdot d^2} \quad \text{max number of single punctures that can be made by the needle}$$

$A = 0.22 \quad \alpha = 38.536 \, \text{deg} \quad a = 3.217 \times 10^{-3} \quad P = 68.473$ Hence, the max number of single punctures is 68. Since a puncture actually produces a semicircular cut in the silicone, the max number of single punctures is roughly 2 x 68 = 136. Note that this calculation neglects the increase in area due to the bulge in the silicone, the actual area is larger than the value of (A) used in this calculation. For test purposes, however, we will use the value of P as calculated using this analysis.

Prototype Scaling

Let's increase the size of the tubing to obtain more puncture area. We will maintain the value of $\alpha$ at 38.536 degrees. In addition, we will maintain the 1/4 inch solid portions at each end of the titanium tubing which contains the silicone tubing and use the same size needle to puncture the silicone.

Silicone tubing is commercially available with an OD = 5/8 in & an ID = 3/8 in. Let's calculate the max number of single punctures for this geometry.

$$\text{Dnew} := .625 \qquad \text{new silicone tubing OD}$$

$$\text{wnew} := \text{Dnew} \cdot \sin(\alpha)$$

$$\text{wnew} = 0.389 \qquad \text{new slot width in the titanium tubing}$$

$$S := \frac{\text{Dnew}}{0.500}$$

$$S = 1.25 \qquad \text{scale factor based on original design}$$

The overall length of the titanium tubing portions in the original prototype is 1.247 inches. The length of the parallel portion of the slot in the titanium tubing of the new prototype, Lnew, is as follows $$\text{Lnew} := 1.247 \cdot S - .5 - \text{wnew}$$

$$\text{Lnew} = 0.669 \qquad \text{length of the parallel portion of the slot}$$

Hence, we can write for Pnew $$\text{Pnew} := \text{wnew} \cdot \frac{(4 \cdot \text{Lnew} + \pi \cdot \text{wnew})}{\pi \cdot d^2}$$

$$\text{Pnew} = 118.034 \qquad \text{max number of single punctures}$$

Hence, the max number of single punctures is 118. The percentage increase, $\Delta$, in the number of punctures over the original prototype is given below $$\Delta := \frac{100 \cdot (\text{Pnew} - P)}{P} \qquad\qquad \text{Anew} := \text{wnew} \cdot \text{Lnew} + \pi \cdot \frac{\text{wnew}^2}{4}$$

$$\Delta = 72.38 \quad \text{percent} \qquad\qquad \text{Anew} = 0.38 \quad \text{in}^2$$

Let's plot the calculated values over a range of silicone diameters from 1/2 to 1 inch OD

Plotting $$\text{Dnew} := \begin{pmatrix} .5 \\ .5625 \\ .625 \\ .6875 \\ .75 \\ .8125 \\ .875 \\ 1 \end{pmatrix} \quad S := \begin{pmatrix} 1 \\ 1.125 \\ 1.25 \\ 1.375 \\ 1.5 \\ 1.625 \\ 1.75 \\ 2 \end{pmatrix} \quad \text{wnew} := \begin{pmatrix} .3115 \\ .35 \\ .389 \\ .428 \\ .467 \\ .506 \\ .545 \\ .623 \end{pmatrix} \quad \text{Lnew} := \begin{pmatrix} .4625 \\ .552 \\ .669 \\ .786 \\ .903 \\ 1.02 \\ 1.137 \\ 1.371 \end{pmatrix} \quad \text{Pnew} := \begin{pmatrix} 68 \\ 90 \\ 118 \\ 149 \\ 184 \\ 223 \\ 265 \\ 360 \end{pmatrix}$$

$$\Delta := \begin{pmatrix} 0 \\ 32.4 \\ 73.5 \\ 119.1 \\ 170.6 \\ 227.9 \\ 289.7 \\ 429.4 \end{pmatrix} \quad \text{Anew} := \begin{pmatrix} .22 \\ .29 \\ .38 \\ .481 \\ .594 \\ .718 \\ .853 \\ 1.159 \end{pmatrix}$$

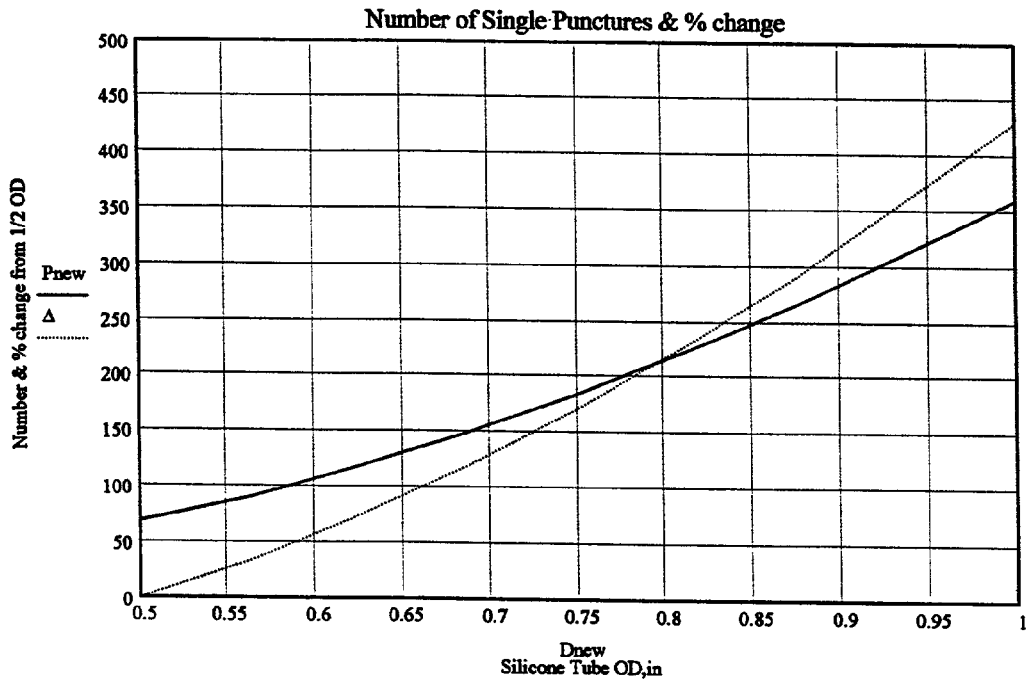

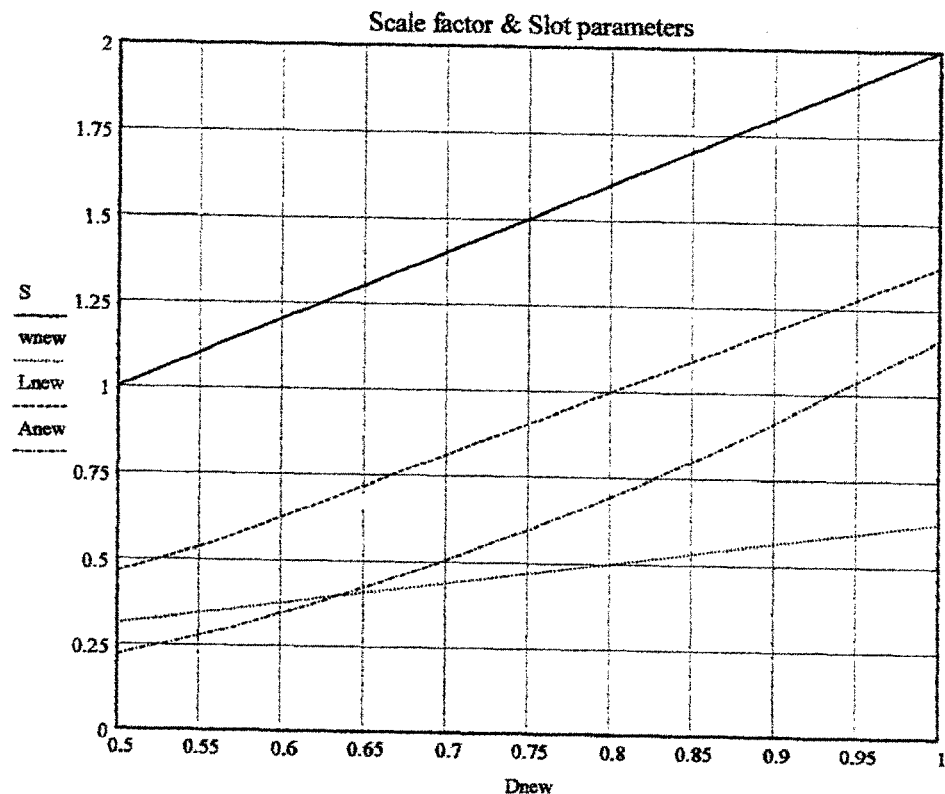
The analysis shows that increasing the OD of the silicone tubing from 1/2 to 1 inch increases the number of single punctures from 68 to 360 which is a percentage increase of 429%. Based on the test results obtained to date using the original prototype with 1/2 inch OD silicone tubing and multiple needle sticks, obtaining 1000 - 2000 needle sticks is definitely feasible.

Length of Slot Modifications

Let's increase the length, L, by 1/4 inch and calculate the number of single punctures. Maintain all other parameters as per the original prototype and increase the overall length of the prototype by 1/4 inch.

$w := .3115$ $L := .7125$ $D := .500$ $d := .064$

Substituting in the equations on page 1, we obtain the following:

$A = 0.298\ in^2 \quad \alpha = 38.536\ deg \quad a = 0.003217\ in^2 \quad P = 92.681$ Hence, by increasing only the value of L from 0.4625 to 0.7125 inches, the number of single punctures is increased from 68 to 92. An increase of 35% in the number of single punctures and the area A.

Testing

Testing of the original prototype to date shows an ability to maintain a no leakage condition of 13 mm Hg after 950 punctures. At 1000 punctures, the leakage pressure drops to 4.4 mm Hg. Based on these results, increasing the length of the original prototype by 1/4 inch should increase the number of punctures to the 1000 to 2000 range at a seal pressure of 13mm Hg. If the overall geometry can be increased further, the number of punctures would be expected to increase beyond 2000 punctures.

The invention claimed is:

1. An implantable dual chambered device, comprising:
a first chamber and a second chamber integrally joined;
the first chamber includes a hollow, cylindrical first elastomeric member contained within a first slotted outer housing, a first end of the first elastomeric member is fitted with a first end cap shaped and dimensioned to accept conventional tubes and the second end of the first elastomeric member is closed;
the second chamber includes a hollow, cylindrical second elastomeric member contained within a second slotted outer housing, a first end of the second elastomeric member is fitted with a second end cap shaped and dimensioned to accept conventional tubes and the second end of the second elastomeric member is closed;
wherein needle access to the first and second chambers of the implantable device is through respective slots formed within the first and second outer housings.

2. The device according to claim 1, wherein the first and second end caps are titanium.

3. The device according to claim 1, wherein the first and second chambers are tubular.

4. The device according to claim 3, wherein the first and second elastomeric members are cylindrical.

5. The device according to claim 3, wherein the first and second slotted outer housings are cylindrical.

6. The device according to claim 5, wherein the first and second elastomeric members are cylindrical.

7. The device according to claim 6, wherein the first and second elastomeric members are respectively held within the first and second outer housings under radial compressive stresses.

8. The device according to claim 5, wherein the first and second slotted outer housings are titanium or other suitable implantable materials.

9. The device according to claim 1, wherein the first and second slotted outer housings are titanium or other suitable implantable materials.

10. The device according to claim 1, wherein the first and second elastomeric members are respectively held within the first and second outer housings under radial compressive stresses.

11. The device according to claim 10, wherein compressive stresses applied to the first and second elastomeric members create a bulge in the first and second elastomeric members along respective slots formed in the first and second outer housings.

12. The device according to claim 11, wherein the compressive stresses are applied circumferential stresses ranging from approximately 6 psi to 87 psi.

13. The device according to claim 10, wherein the radial compressive stresses applied to the first and second elastomeric members provide compressive circumferential hoop stresses in the first and second elastomeric member which serve to seal needle holes in the first and second elastomeric members following needle withdrawal.

14. The device according to claim 10, wherein applied circumferential stresses range from approximately 6 psi to 87 psi.

15. The device according to claim 10, wherein the first and second elastomeric members include uncompressed outer dimensions slightly larger than the inner dimensions of the respective first and second outer housings in which they are positioned.

16. The device according to claim 1, wherein the first and second elastomeric members include uncompressed outer dimensions slightly larger than the inner dimensions of the respective first and second outer housings in which they are positioned.

17. The device according to claim 1, wherein the first and second elastomeric members are constructed from implantable grade silicone rubber or suitable implantable elastomeric materials.

18. The device according to claim 1, wherein the first and second elastomeric members have a preferred durometer of 60 Shore A.

19. The device according to claim 11, wherein the compressive stresses applied to the first and second elastomeric members provide compressive hoop stresses sufficient to seal needle puncture holes in the elastomeric members.

20. The device according to claim 19, wherein the compressive stresses include stresses applied to the first and second elastomeric members by the first and second end caps to increase the size of the bulge in the first and second elastomeric members.

* * * * *